United States Patent
Ben-David et al.

(10) Patent No.: US 8,036,745 B2
(45) Date of Patent: Oct. 11, 2011

(54) PARASYMPATHETIC PACING THERAPY DURING AND FOLLOWING A MEDICAL PROCEDURE, CLINICAL TRAUMA OR PATHOLOGY

(75) Inventors: Tamir Ben-David, Tel Aviv (IL); Omry Ben-Ezra, Jerusalem (IL); Ehud Cohen, Ganei Tikva (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 1022 days.

(21) Appl. No.: 11/359,266

(22) Filed: Feb. 21, 2006

(65) Prior Publication Data

US 2006/0206155 A1 Sep. 14, 2006

Related U.S. Application Data

(63) Continuation-in-part of application No. 10/866,601, filed on Jun. 10, 2004.

(60) Provisional application No. 60/655,604, filed on Feb. 22, 2005.

(51) Int. Cl.
*A61N 1/18* (2006.01)
(52) U.S. Cl. .................. 607/9; 607/2; 607/40; 607/116; 607/118; 607/133
(58) Field of Classification Search .................. 607/2, 9, 607/40, 116, 118, 133
See application file for complete search history.

(56) References Cited

U.S. PATENT DOCUMENTS

| | | | |
|---|---|---|---|
| 5,058,599 | A | 10/1991 | Anderson |
| 5,139,020 | A | 8/1992 | Koestner et al. |
| 5,615,684 | A | 4/1997 | Hagel et al. |
| 6,058,328 | A | 5/2000 | Levine et al. |
| 6,104,956 | A | 8/2000 | Naritoku et al. |
| 6,195,584 | B1 | 2/2001 | Hill et al. |
| 6,473,644 | B1 | 10/2002 | Terry et al. |
| 6,522,926 | B1 | 2/2003 | Kieval et al. |
| 6,571,122 | B2 | 5/2003 | Schroeppel et al. |
| 6,622,041 | B2 | 9/2003 | Terry et al. |

(Continued)

FOREIGN PATENT DOCUMENTS

WO WO 2006/102370 9/2006

OTHER PUBLICATIONS

Armour, J. et al., (1994) "Neurocardiology", *Oxford University Press* pp. 60-64.

(Continued)

*Primary Examiner* — Carl H Layno
*Assistant Examiner* — Deborah Malamud
(74) *Attorney, Agent, or Firm* — Sughrue Mion, PLLC

(57) ABSTRACT

A treatment method is provided, including identifying a subject as one who is selected to undergo an interventional medical procedure, and, in response to the identifying, reducing a likelihood of a potential adverse effect of the procedure by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

23 Claims, 4 Drawing Sheets

U.S. PATENT DOCUMENTS

| | | | |
|---|---|---|---|
| 6,690,971 | B2 | 2/2004 | Schauerte et al. |
| 6,885,888 | B2 | 4/2005 | Rezai et al. |
| 7,136,700 | B1 | 11/2006 | Province et al. |
| 7,403,819 | B1 | 7/2008 | Shelchuk et al. |
| 7,509,166 | B2 * | 3/2009 | Libbus ............................ 607/9 |
| 7,765,000 | B2 | 7/2010 | Zhang et al. |
| 2004/0172075 | A1 * | 9/2004 | Shafer et al. ...................... 607/9 |
| 2006/0047325 | A1 | 3/2006 | Thimineur et al. |
| 2006/0064140 | A1 | 3/2006 | Whitehurst et al. |
| 2006/0149337 | A1 | 7/2006 | John |
| 2006/0167498 | A1 | 7/2006 | DiLorenzo |
| 2006/0259077 | A1 | 11/2006 | Pardo et al. |

OTHER PUBLICATIONS

Billette, J. et al., (1975) "Roles of the AV junction in determining the ventricular response to atrial fibrillation," *Canadian Journal of Physiology and Pharmacology* 53(4):575-85 (1975).

Borovikova, L. et al., (2000) "Vagus nerve stimulation attenuates the systemic inflammatory response to endotoxin," *Nature* 405(6785):458-62.

Cummings, J. et al., (2004) "Preservation of the anterior fat pad paradoxically decreases the incidence of postoperative atrial fibrillation in humans," *Journal of the American College of Cardiology* 43(6):994-1000.

De Ferrari, G. et al. (1991) "Vagal reflexes and survival during acute myocardial ischemia in conscious dogs with healed myocardial infarction," *American Journal of Physiology* 261(1 Pt 2):H63-9.

Feliciano, L et al., (1998) "Vagal nerve stimulation releases vasoactive intestinal peptide which significantly increases coronary artery blood flow," *Cardiovascular Research* 40:45-55.

Garrigue, S. et al., (1998) "Post-ganglionic vagal stimulation of the atrioventricular node reduces ventricular rate during atrial fibrillation," PACE 21(4, Part II):356.

Hayash,i H. et al., (1998) "Different effects of class Ic and III antiarrhythmic drugs on vagotonic atrial fibrillation in the canine heart," *Journal of Cardiovascular Pharmacology* 31:101-107.

Higgins, C., (1973) "Parasympathetic control of the heart," *Pharmacological Review* 25:120-155.

Jideus, L,. (2001) "Atrial fibrillation after coronary artery bypass surgery: A study of causes and risk factors," *Acta Universitatis Upsaliensis* 1-56.

Jones, J. et al., (1995) "Heart rate responses to selective stimulation of cardiac vagal C fibres in anaesthetized cats, rats and rabbits," *Journal of Physiology* 489 (1):203-14.

Kwan, H. et al., (2001) "Cardiovascular adverse drug reactions during initiation of antiarrhythmic therapy for atrial fibrillation," *Canadian Journal of Hospital* Pharmacy 54(1):10-14.

Li, D. et al., (1999) "Promotion of Atrial Fibrillation by Heart Failure in Dogs: Atrial Remodeling of a Different Sort," *Circulation* 100(1):87-95.

Lindmark, S. et al., (2003) "Does the autonomic nervous system play a role in the development of insulin resistance? A study on heart rate variability in first-degree relatives of type 2 diabetes patients and control subjects." *Diabetes Medicine* 20:399-405.

Martin, P. et al., (1983) "Phasic effects of repetitive vagal stimulation on atrial contraction," *Circulation Research*. 52(6):657-663.

Morady, F. et al., (1990) "Effects of resting vagal tone on accessory atrioventricular connections," *Circulation* 81(1):86-90.

Randall, W. et al., (1977) "Neural Regulation of the Heart," *Oxford University Press* pp. 100-106.

Stramba-Badiale, M. et al., (1991) "Sympathetic-Parasympathetic Interaction and Accentuated Antagonism in Conscious Dogs," *American Journal of Physiology* 260 (2Pt 2):H335-340.

Svedjeholm, R. et al., (2000) "Predictors of atrial fibrillation in patients undergoing surgery for ischemic heart disease," Scandanavian. *Cardiovascular Journal* 34:516-21.

Takei, M. et al., (2001) "Vagal stimulation prior to atrial rapid pacing protects the atrium from electrical remodeling in anesthetized dogs," *Japanese Circulation* Journal 65(12):1077-81.

Takayama, S. et al., (2001) "A possible involvement of parasympathetic neuropathy on insulin resistance in patients with type 2 diabetes," *Diabetes Care* 24(5):968-969.

Vanoli, E. et al., (1991) "Vagal stimulation and prevention of sudden death in conscious dogs with a healed myocardial infarction," *Circulation Research* 68(5): 1471-1481.

Wang, H. et al., (Jan. 23, 2003) "Nicotinic acetylcholine receptor alpha-7 subunit is an essential regulator of inflammation," *Nature* 421:384-388.

Waninger, M. et al., (2000) "Electrophysiological control of ventricular rate during atrial fibrillation," *PACE* 23:1239-1244.

Wijffels, M. et al., (1995) "Atrial fibrillation begets atrial fibrillation," *Circulation* 92:1954-1968.

Zhang, Y. et al., (2002) "Optimal ventricular rate slowing during atrial fibrillation by feedback AV nodal-selective vagal stimulation," *American Journal of Physiology and Heart Circulatory and Physiology* 282:H1102-H1110.

Oct. 29, 2007 Final Office Action issued in connection with U.S. Appl. No. 10/866,601.

Schaldach, M., (1992) "New Concepts in Electrotherapy of the Heart," Electrotherapy of the Heart, Springer Verlag Heidelberg: 210-214.

Office Action, issued Jun. 24, 2009, in connection with U.S. Appl. No. 11/978,379, filed Oct. 29, 2007.

Office Action, issued Aug. 21, 2009, in connection with U.S. Appl. No. 11/975,240, filed Oct. 17, 2007.

Office Action, issued Aug. 25, 2009, in connection with U.S. Appl. No. 11/975,241, filed Oct. 17, 2007.

Morillo et al., "Chronic Rapid Atrial Pacing. Structural, functional, and electrophysiological characteristics of a new model of sustained atrial fibrillation," *Circulation*, 1995, 91(5), 1588-1595.

Office Action, issued Feb. 5, 2010, in connection with U.S. Appl. No. 11/974,951, filed Oct. 16, 2007.

Office Action, issued Oct. 12, 2010 in connection with U.S. Appl. No. 11/974,951, filed Oct. 16, 2007.

Office Action, issued Oct. 27, 2010 in connection with U.S. Appl. No. 11/977,291, filed Oct. 23, 2007.

U.S. non-final Office Action for corresponding U.S. Appl. No. 11/974,951 mailed Feb. 4, 2011.

* cited by examiner

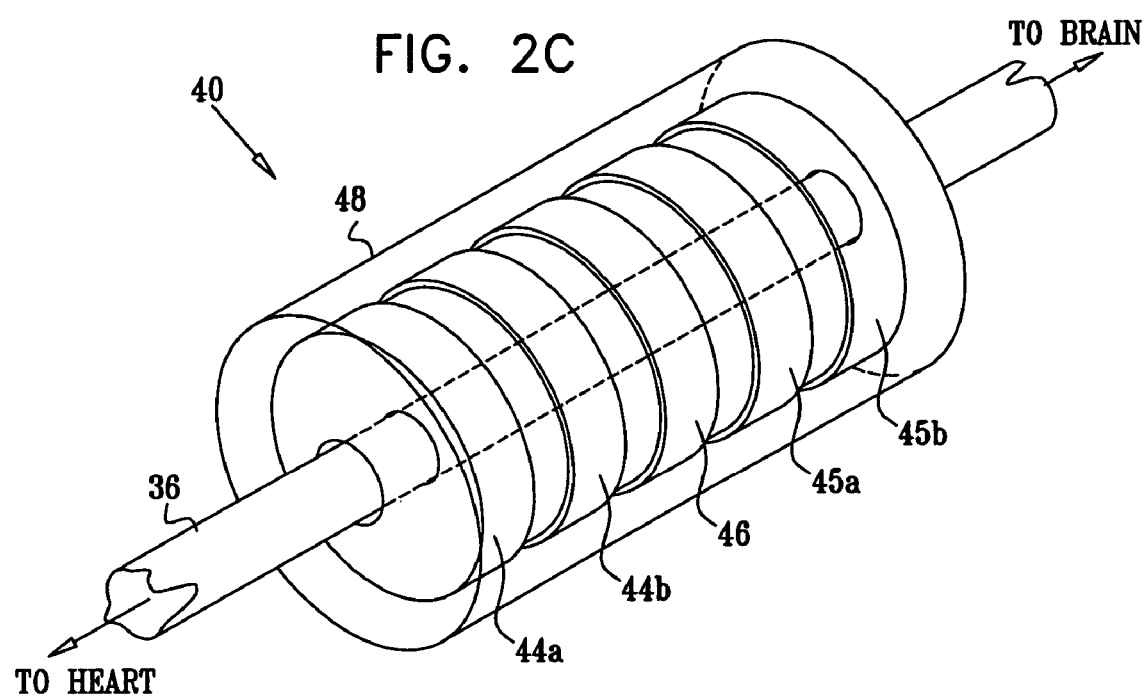

PARASYMPATHETIC PACING THERAPY DURING AND FOLLOWING A MEDICAL PROCEDURE, CLINICAL TRAUMA OR PATHOLOGY

CROSS-REFERENCES TO RELATED APPLICATIONS

The present application (a) claims the benefit of U.S. Provisional Patent Application 60/655,604, filed Feb. 22, 2005, entitled, "Techniques for applying, calibrating, and controlling nerve fiber stimulation," and (b) is a continuation-in-part of U.S. patent application Ser. No. 10/866,601, filed Jun. 10, 2004, entitled, "Applications of vagal stimulation." Both of these applications are assigned to the assignee of the present application and incorporated herein by reference.

FIELD OF THE INVENTION

The present invention relates generally to treating subjects by application of electrical signals to selected tissue, and specifically to methods and apparatus for applying parasympathetic stimulation to selected tissue for treating and/or preventing various medical disorders.

BACKGROUND OF THE INVENTION

The use of nerve stimulation for treating and controlling a variety of medical, psychiatric, and neurological disorders has seen significant growth over the last several decades, including for treatment of heart conditions. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic stimulation from the right and left vagus nerves. Low vagal nerve activity is considered to be related to various arrhythmias, including tachycardia, ventricular accelerated rhythm, and rapid atrial fibrillation. Stimulation of the vagus nerve has been proposed as a method for treating various heart conditions, including atrial fibrillation and heart failure. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Atrial fibrillation (AF) is a condition in which the atria of the heart fail to continuously contract in synchrony with the ventricles of the heart. During fibrillation, the atria undergo rapid and unorganized electrical depolarization, so that no contractile force is produced. The ventricles, which normally receive contraction signals from the atria (through the atrioventricular (AV) node), are inundated with signals, typically resulting in a rapid and irregular ventricular rate. Because of this rapid and irregular rate, the patient suffers from reduced cardiac output, a feeling of palpitations, and/or increased risk of thromboembolic events.

Current therapy for atrial fibrillation includes cardioversion and rate control. Cardioversion is the conversion of the abnormal atrial rhythm into normal sinus rhythm. This conversion is generally achieved pharmacologically or electrically. Rate control therapy is used to control the ventricular rate, while allowing the atria to continue fibrillation. This is generally achieved by slowing the conduction of signals through the AV node from the atria to the ventricles.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats. The authors further studied the use of the implanted device in conjunction with the administration of Isuprel, a sympathomimetic drug. They found that Isuprel retained its inotropic effect of increasing contractility, while its chronotropic effect was controlled by the vagal stimulation: "An increased end diastolic volume brought about by slowing of the heart rate by vagal tuning, coupled with increased contractility of the heart induced by the inotropic effect of Isuprel, appeared to increase the efficiency of cardiac performance" (p. 79).

Svedjeholm R et al., in "Predictors of atrial fibrillation in patients undergoing surgery for ischemic heart disease," Scand Cardiovasc J 34:516-21 (2000), which is incorporated herein by reference, analyze risk factors for postoperative AF in a uniformly managed cohort of patients. The authors report that the incidence of AF was 29.1% in patients undergoing isolated CABG and 48.6% after CABG+valve procedures.

Cummings J E et al., in "Preservation of the anterior fat pad paradoxically decreases the incidence of postoperative atrial fibrillation in humans," J Am Coll Cardiol 43(6):994-1000 (2004), which is incorporated herein by reference, describe a study they performed to determine if parasympathetic nerves in the anterior fat pad can be stimulated at the time of coronary artery bypass graft (CABG) surgery, and if dissection of this fat pad decreases the incidence of postoperative atrial fibrillation (AF). The authors report that direct stimulation of the anterior epicardial fat pad slows sinus cycle length, and that this parasympathetic effect is eliminated with fat pad dissection. They conclude that the preservation of the human anterior epicardial fat pad during CABG surgery decreases the incidence of postoperative AF.

An article by Moreira et al., entitled, "Chronic rapid atrial pacing to maintain atrial fibrillation: Use to permit control of ventricular rate in order to treat tachycardia induced cardiomyopathy," Pacing Clin Electrophysiol, 12(5):761-775 (May 1989), which is incorporated herein by reference, describes the acute induction of atrial fibrillation with rapid atrial pacing, and an associated reduction in ventricular rate with digitalis therapy. Different treatment protocols are described to induce and maintain atrial fibrillation, in order to bring a patient with NYHA class III-IV congestive heart failure to a more moderate NYHA class II.

An article by Preston et al., entitled, "Permanent rapid atrial pacing to control supraventricular tachycardia," Pacing Clin Electrophysiol, 2(3):331-334 (May 1979), which is incorporated herein by reference, describes a patient who had continuous supraventricular tachycardia with a ventricular rate of about 170. The arrhythmia was refractory to drugs and DC countershock, and did not convert with atrial pacing. Rapid atrial stimulation (pacing at 300-400/min) controlled the ventricular rate by simulating atrial fibrillation. This therapy was used on a permanent basis for more than five months.

An article by Lindmark S. et al., entitled, "Does the autonomic nervous system play a role in the development of insulin resistance? A study on heart rate variability in first-degree relatives of type 2 diabetes patients and control subjects." Diabet Med 20:399-405, 2003, which is incorporated herein by reference, describes how vagal activity is correlated with insulin resistance.

U.S. Pat. No. 6,473,644 to Terry, Jr. et al., which is incorporated herein by reference, describes a method for treating patients suffering from heart failure to increase cardiac output, by stimulating or modulating the vagus nerve with a sequence of substantially equally-spaced pulses by an implanted neurostimulator. The frequency of the stimulating pulses is adjusted until the patient's heart rate reaches a target rate within a relatively stable target rate range below the low end of the patient's customary resting heart rate.

The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

The following articles and book, which are incorporated herein by reference, may be of interest:

Levy M N et al., in "Parasympathetic Control of the Heart," *Nervous Control of Vascular Function*, Randall W C ed., Oxford University Press (1984)

Levy M N et al. ed., Vagal Control of the Heart: Experimental Basis and Clinical Implications (The Bakken Research Center Series Volume 7), Futura Publishing Company, Inc., Armonk, N.Y. (1993)

Randall W C ed., *Neural Regulation of the Heart*, Oxford University Press (1977), particularly pages 100-106.

Armour J A et al. eds., *Neurocardiology*, Oxford University Press (1994)

Perez M G et al., "Effect of stimulating non-myelinated vagal axon on atrioventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," Am J Physiol 237(3):H275-81 (1979)

Fuster V and Ryden L E et al., "ACC/AHA/ESC Practice Guidelines—Executive Summary," J Am Coll Cardiol 38(4):1231-65 (2001)

Fuster V and Ryden L E et al., "ACC/AHA/ESC Practice Guidelines—Full Text," J Am Coll Cardiol 38(4):1266i-12661xx (2001)

Morady F et al., "Effects of resting vagal tone on accessory atrioventricular connections," Circulation 81(1):86-90 (1990)

Waninger M S et al., "Electrophysiological control of ventricular rate during atrial fibrillation," PACE 23:1239-1244 (2000)

Wijffels M C et al., "Electrical remodeling due to atrial fibrillation in chronically instrumented conscious goats: roles of neurohumoral changes, ischemia, atrial stretch, and high rate of electrical activation," Circulation 96(10):3710-20 (1997)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Lew S J et al., "Stroke prevention in elderly patients with atrial fibrillation," Singapore Med J 43(4):198-201 (2002)

Higgins C B, "Parasympathetic control of the heart," Pharmacol. Rev. 25:120-155 (1973)

Hunt R, "Experiments on the relations of the inhibitory to the accelerator nerves of the heart," J. Exptl. Med. 2:151-179 (1897)

Billette J et al., "Roles of the AV junction in determining the ventricular response to atrial fibrillation," Can J Physiol Pharamacol 53(4)575-85 (1975)

Stramba-Badiale M et al., "Sympathetic-Parasympathetic Interaction and Accentuated Antagonism in Conscious Dogs," American Journal of Physiology 260 (2 Pt 2):H335-340 (1991)

Garrigue S et al., "Post-ganglionic vagal stimulation of the atrioventricular node reduces ventricular rate during atrial fibrillation," PACE 21(4), 878 (Part II) (1998)

Kwan H et al., "Cardiovascular adverse drug reactions during initiation of antiarrhythmic therapy for atrial fibrillation," Can J Hosp Pharm 54:10-14 (2001)

Jidéus L, "Atrial fibrillation after coronary artery bypass surgery: A study of causes and risk factors," Acta Universitatis Upsaliensis, Uppsala, Sweden (2001)

Borovikova L V et al., "Vagus nerve stimulation attenuates the systemic inflammatory response to endotoxin," Nature 405(6785):458-62 (2000)

Wang H et al., "Nicotinic acetylcholine receptor alpha-7 subunit is an essential regulator of inflammation," Nature 421:384-388 (2003)

Vanoli E et al., "Vagal stimulation and prevention of sudden death in conscious dogs with a healed myocardial infarction," Circ Res 68(5):1471-81 (1991)

De Ferrari G M, "Vagal reflexes and survival during acute myocardial ischemia in conscious dogs with healed myocardial infarction," Am J Physiol 261(1 Pt 2):H63-9 (1991)

Li D et al., "Promotion of Atrial Fibrillation by Heart Failure in Dogs: Atrial Remodeling of a Different Sort," Circulation 100(1):87-95 (1999)

Feliciano L et al., "Vagal nerve stimulation during muscarinic and beta-adrenergic blockade causes significant coronary artery dilation," Cardiovasc Res 40(1):45-55 (1998)

Lindmark S et al., "Does the autonomic nervous system play a role in the development of insulin resistance? A study on heart rate variability in first-degree relatives of type 2 diabetes patients and control subjects," Diabet Med 20:399-405 (2003)

Takayama S et al., "A possible involvement of parasympathetic neuropathy on insulin resistance in patients with type 2 diabetes," Diabetes Care 24:968-969 (2001)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

U.S. Pat. No. 5,330,507 to Schwartz, which is incorporated herein by reference, describes a cardiac pacemaker for preventing or interrupting tachyarrhythmias and for applying pacing therapies to maintain the heart rhythm of a patient within acceptable limits. The device automatically stimulates the right or left vagus nerves as well as the cardiac tissue in a concerted fashion dependent upon need. Continuous and/or phasic electrical pulses are applied. Phasic pulses are applied in a specific relationship with the R-wave of the ECG of the patient.

European Patent Application EP 0 688 577 to Holmström et al., which is incorporated herein by reference, describes a device to treat atrial tachyarrhythmia by detecting arrhythmia and stimulating a parasympathetic nerve that innervates the heart, such as the vagus nerve.

U.S. Pat. Nos. 5,690,681 and 5,916,239 to Geddes et al., which are incorporated herein by reference, describe closed-loop, variable-frequency, vagal-stimulation apparatus for control of ventricular rate during atrial fibrillation. The apparatus stimulates the left vagus nerve, and automatically and continuously adjusts the vagal stimulation frequency as a function of the difference between actual and desired ventricular excitation rates. In an alternative embodiment, the apparatus automatically adjusts the vagal stimulation frequency as a function of the difference between ventricular excitation rate and arterial pulse rate in order to eliminate or minimize pulse deficit.

US Patent Application Publication 2003/0040774 to Terry et al., which is incorporated herein by reference, describes a device for treating patients suffering from congestive heart failure. The device includes an implantable neurostimulator for stimulating the patient's vagus nerve at or above the cardiac branch with an electrical pulse waveform at a stimulating rate sufficient to maintain the patient's heart beat at a rate well below the patient's normal resting heart rate, thereby allowing rest and recovery of the heart muscle, to increase in coronary blood flow, and/or growth of coronary capillaries. A metabolic need sensor detects the patient's current physical state and concomitantly supplies a control signal to the neurostimulator to vary the stimulating rate. If the detection indicates a state of rest, the neurostimulator rate reduces the patient's heart rate below the patient's normal resting rate. If the detection indicates physical exertion, the neurostimulator rate increases the patient's heart rate above the normal resting rate.

US Patent Publication 2003/0045909 to Gross et al., which is assigned to the assignee of the present patent application and is incorporated herein by reference, describes apparatus for treating a heart condition of a subject, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

US Patent Publication 2003/0229380 to Adams et al., which is incorporated herein by reference, describes techniques for electrically stimulating the right vagus nerve in order to reduce the heart rate of a patient suffering from conditions such as chronic heart failure, ischemia, or acute myocardial infarction. The amount of energy of the stimulation may be determined in accordance with a difference between the patient's actual heart rate and a maximum target heart rate for the patient. Delivery of energy is preferably synchronized with the detection of a P-wave. Automatic adjustment of the target heart rate may be based on current day and/or time of day information, and patient physical activity. The voltage, pulse width, or number of pulses in the stimulation may be controlled.

US Patent Application Publication 2005/0154419 to Whitehurst et al., which is incorporated herein by reference, describes methods for treating a medical condition, including applying at least one stimulus to a target nerve within the patient with an implanted system control unit in accordance with one or more stimulation parameters. The target nerve may include any nerve originating in an upper cervical spine area of the patient or a branch of any nerve originating in the upper cervical spine area of the patient. Medical conditions described include cerebrovascular disease, an autoimmune disease, a sleep disorder (e.g., sleep apnea), an autonomic disorder, a urinary bladder disorder, epilepsy, hyperthyroidism, hypothyroidism, a muscular system disorder, a neuropsychiatric disorder (e.g., depression, schizophrenia, bipolar disorder, autism, personality disorders, and obsessive-compulsive disorder), pain, a gastrointestinal disorder (e.g., a gastrointestinal motility disorder, nausea, vomiting, diarrhea, chronic hiccups, gastroesophageal reflux disease, and hypersecretion of gastric acid), autonomic insufficiency, excessive epiphoresis, excessive rhinorrhea, and a cardiovascular disorder (e.g., cardiac dysrhythmias and arrhythmias, hypertension, and carotid sinus disease).

U.S. Pat. No. 6,526,318 to Ansarinia, which is incorporated herein by reference, describes a method for the suppression or prevention of pain, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders in a patient. The method comprises positioning at least one electrode on or proximate to at least one of the patient's sphenopalatine ganglia ("SPG"), sphenopalatine nerves ("SPN"), or vidian nerves ("VN"), and activating the at least one electrode to apply an electrical signal to at least one of the SPG, SPN, or VN. In a further embodiment, a method is described to treat the same conditions, and the electrode used is capable of dispensing a medication solution or analgesic which is applied via an electrode to at least one of the SPG, SPN, or VN. A method is also provided for surgically implanting an electrode on or proximate to at least one of the SPG, SPN, or VN of a patient. A method for treating hiccups is also described.

US Patent Application Publication 2005/0080458 to Ehlinger, Jr. et al., which is incorporated herein by reference, describes a device for the treatment of hiccups, and more specifically, a method and apparatus for the treatment of hiccups involving galvanic stimulation of the superficial phrenic and vagus nerves using an electric current.

U.S. Pat. No. 5,188,104 to Wernicke et al., which is incorporated herein by reference, describes a method for treating patients with compulsive eating disorders includes the steps of detecting a preselected event indicative of an imminent need for treatment of the specific eating disorder of interest, and responding to the detected occurrence of the preselected event by applying a predetermined stimulating signal to the patient's vagus nerve appropriate to alleviate the effect of the eating disorder of interest. For example, the preselected event may be a specified level of food consumption by the patient within a set interval of time, or the commencement of a customary mealtime according to the patient's circadian cycle, or the passage of each of a sequence of preset intervals of time, or the patient's own recognition of the need for treatment by voluntarily initiating the application of the stimulating signal to the vagus nerve. In cases in which the disorder is compulsive eating to excess, the stimulating signal is predetermined to produce a sensation of satiety in the patient. The occurrence of the preselected event is detected by summing the number of swallows of food by the patient within the set interval of time. In cases where the disorder is compulsive refusal to eat (anorexia nervosa), the stimulating signal is predetermined to produce a sensation of hunger or to suppress satiety in the patient.

U.S. Pat. No. 5,540,734 to Zabara, which is incorporated herein by reference, describes the treatment, control or prevention of medical, psychiatric or neurological disorders accomplished by application of modulating electric signals to one or both of a patient's trigeminal and glossopharyngeal nerves. The disorders treatable, controllable or preventable by such nerve stimulation are described as including voluntary and involuntary disorders, migraine, epileptic seizure, motor disorders, Parkinson's disease, cerebral palsy, spasticity, chronic nervous illnesses and involuntary movement; pancreatic endocrine disorders including diabetes and hypoglycemia; dementia including cortical, subcortical, multi-infarct, Alzheimer's disease and Pick's disease; sleep disorders including central sleep apnea, insomnia and hypersomnia; eating disorders including anorexia nervosa, bulimia and compulsive overeating; and neuropsychiatric disorders including schizophrenia, depression and borderline personality disorder.

PCT Patent Publication WO 2001/85094 to Shalev et al., which is incorporated herein by reference, describes apparatus for modifying a property of a brain of a patient is provided, including one or more electrodes, adapted to be applied to a site selected from a group of sites consisting of: a sphenopalatine ganglion (SPG) of the patient and a neural tract originating in or leading to the SPG. A control unit is adapted to drive the one or more electrodes to apply a current to the site capable of inducing (a) an increase in permeability of a blood-brain barrier (BBB) of the patient, (b) a change in cerebral blood flow of the patient, and/or (c) an inhibition of parasympathetic activity of the SPG.

U.S. Pat. No. 5,203,326 to Collins, which is incorporated herein by reference, describes a pacemaker which detects a cardiac abnormality and responds with electrical stimulation of the heart combined with vagus nerve stimulation. The vagal stimulation frequency is progressively increased in one-minute intervals, and, for the pulse delivery rate selected, the heart rate is described as being slowed to a desired, stable level by increasing the pulse current.

U.S. Pat. No. 6,511,500 to Rahme, which is incorporated herein by reference, describes various aspects of the effects of autonomic nervous system tone on atrial arrhythmias, and its interaction with class III antiarrhythmic drug effects.

U.S. Pat. No. 5,199,428 to Obel et al., which is incorporated herein by reference, describes a cardiac pacemaker for detecting and treating myocardial ischemia. The device automatically stimulates the vagal nervous system as well as the cardiac tissue in a concerted fashion in order to decrease cardiac workload and thereby protect the myocardium.

U.S. Pat. Nos. 5,334,221 to Bardy and 5,356,425 to Bardy et al., which are incorporated herein by reference, describe a stimulator for applying stimulus pulses to the AV nodal fat pad in response to the heart rate exceeding a predetermined rate, in order to reduce the ventricular rate. The device also includes a cardiac pacemaker which serves to pace the ventricle in the event that the ventricular rate is lowered below a pacing rate, and provides for feedback control of the stimulus parameters applied to the AV nodal fat pad, as a function of the determined effect of the stimulus pulses on the heart rate.

U.S. Pat. No. 5,522,854 to Ideker et al., which is incorporated herein by reference, describes techniques for preventing arrhythmia by detecting a high risk of arrhythmia and then stimulating afferent nerves to prevent the arrhythmia.

U.S. Pat. No. 6,434,424 to Igel et al., which is incorporated herein by reference, describes a pacing system with a mode switching feature and ventricular rate regularization function adapted to stabilize or regularize ventricular heart rate during chronic or paroxysmal atrial tachyarrhythmia.

US Patent Application Publication 2002/0120304 to Mest, which is incorporated herein by reference, describes a method for regulating the heart rate of a patient by inserting into a blood vessel of the patient a catheter having an electrode at its distal end, and directing the catheter to an intravascular location so that the electrode is adjacent to a selected cardiac sympathetic or parasympathetic nerve.

U.S. Pat. Nos. 6,006,134 and 6,266,564 to Hill et al., which are incorporated herein by reference, describe an electrostimulation device including a pair of electrodes for connection to at least one location in the body that affects or regulates the heartbeat.

PCT Publication WO 02/085448 to Foreman et al., which is incorporated herein by reference, describes a method for protecting cardiac function and reducing the impact of ischemia on the heart, by electrically stimulating a neural structure capable of carrying the predetermined electrical signal from the neural structure to the "intrinsic cardiac nervous system," which is defined and described therein.

U.S. Pat. No. 5,243,980 to Mehra, which is incorporated herein by reference, describes techniques for discrimination between ventricular and supraventricular tachycardia. In response to the detection of the occurrence of a tachycardia, stimulus pulses are delivered to one or both of the SA and AV nodal fat pads. The response of the heart rhythm to these stimulus pulses is monitored. Depending upon the change or lack of change in the heart rhythm, a diagnosis is made as to the origin of the tachycardia.

U.S. Pat. No. 5,658,318 to Stroetmann et al., which is incorporated herein by reference, describes a device for detecting a state of imminent cardiac arrhythmia in response to activity in nerve signals conveying information from the autonomic nerve system to the heart. The device comprises a sensor adapted to be placed in an extracardiac position and to detect activity in at least one of the sympathetic and vagus nerves.

U.S. Pat. No. 6,292,695 to Webster, Jr. et al., which is incorporated herein by reference, describes a method for controlling cardiac fibrillation, tachycardia, or cardiac arrhythmia by the use of a catheter comprising a stimulating electrode, which is placed at an intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

U.S. Pat. No. 6,134,470 to Hartlaub, which is incorporated herein by reference, describes an implantable anti-arrhythmia system which includes a spinal cord stimulator coupled to an implantable heart rhythm monitor. The monitor is adapted to detect the occurrence of tachyarrhythmias or of precursors thereto and, in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation.

US Patent Application Publication 2003/0181958 to Dobak, which is incorporated herein by reference, describes a method for the treatment of obesity or other disorders, by electrical activation or inhibition of the sympathetic nervous system. This activation or inhibition is achieved by electrically stimulating the greater splanchnic nerve or another portion of the sympathetic nervous system using an implantable pulse generator. This nerve activation is described as possibly resulting in reduced food intake and increased energy expenditure. Reduced food intake is described as possibly occurring through a variety of mechanisms that reduce appetite and cause satiety. Increased adrenal gland hormone levels are described as resulting in increased energy expenditure. Fat and carbohydrate metabolism, which are described as being increased by sympathetic nerve activation, are described as accompanying the increased energy expenditure.

U.S. Pat. No. 5,335,657 to Terry, Jr. et al., which is incorporated herein by reference, describes techniques for treating and controlling sleep disorders by detecting the presence of the sleep disorder under treatment, and, in response, selectively applying a predetermined electrical signal to the patient's vagus nerve for stimulation thereof to alleviate the sleep disorder under treatment. The method and apparatus includes several techniques for detecting the presence of the sleep disorder under treatment, such as sensing the patient's EEG activity in the case of insomniac and hypersomniac patients, or detecting a sudden nodding of the head in the case of narcoleptic patients, or sensing the cessation of respiration in the case of sleep apnea patients.

PCT Publication WO 04/078252 to Karashurov, which is incorporated herein by reference, describes an implanted system for treatment of human diseases by electric stimulation and/or electric blocking of the body tissues, comprising sensor and/or biosensor means for measuring variables in the body, processor means connected to the sensors and biosensors for processing the measured variables and for deciding in real time whether to apply an electric signal to the body tissues, and electrode means implanted at predefined locations and connected to the processor means, for applying the stimulation and/or electric blocking signals to the body tissues.

U.S. Pat. No. 6,668,191 to Boveja, which is incorporated herein by reference, describes apparatus for neuromodulation adjunct (add-on) therapy for atrial fibrillation, refractory hypertension, and inappropriate sinus tachycardia, comprising an implantable lead-receiver and an external stimulator. Neuromodulation is performed using pulsed electrical stimulation. The external stimulator contains a primary coil which inductively transfers electrical signals to the implanted lead-receiver, which is also in electrical contact with a vagus nerve. The external stimulator emits electrical pulses to stimulate the vagus nerve according to a predetermined program. In a second mode of operation, an operator may manually override the predetermined sequence of stimulation.

A number of patents and articles describe other methods and devices for stimulating nerves to achieve a desired effect. Often these techniques include a design for an electrode or electrode cuff.

US Patent Publication 2003/0050677 to Gross et al., which is assigned to the assignee of the present patent application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

U.S. Pat. No. 4,608,985 to Crish et al. and U.S. Pat. No. 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode. The current applied to the electrodes blocks nerve transmission, but, as described, does not activate the nerve fibers in either direction.

U.S. Pat. No. 6,600,956 to Maschino et al., which is incorporated herein by reference, describes an electrode assembly to be installed on a patient's nerve. The electrode assembly has a thin, flexible, electrically insulating circumneural carrier with a split circumferential configuration longitudinally attached to a lead at the distal end thereof. The carrier possesses circumferential resiliency and has at least one flexible, elastic electrode secured to the underside thereof and electrically connected to an electrical conductor in said lead. A fastener serves to close the split configuration of the carrier to prevent separation from the nerve after installation of the electrode assembly onto the nerve. Tear away webbing secured to adjacent serpentine segments of the lead near the carrier enables the lead to lengthen with patient movements.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33(6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Manfredi M, "Differential block of conduction of larger fibers in peripheral nerve by direct current," Arch. Ital. Biol., 108:52-71 (1970)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j,$$

where U is the potential, σ is the conductance tensor specifying the conductance of the various materials (electrode housing, axon, intracellular fluid, etc.), and j is a scalar function representing the current source density specifying the locations of current injection.

SUMMARY OF THE INVENTION

In some embodiments of the present invention, apparatus for applying vagal stimulation to a patient comprises a control unit and an electrode device, which is applied to a portion of a vagus nerve in order to increase parasympathetic tone of the patient, for example, in order to increase parasympathetic tone with respect to parasympathetic innervation of the heart of the patient. For some applications, the electrode device is applied to a portion of the vagus nerve that innervates the heart. The apparatus is adapted to be used prior to, during, and/or following a clinical procedure. The control unit drives the electrode device to apply vagal stimulation, and typically configures the stimulation to reduce a potential immune-mediated response to the procedure. Such a reduction generally promotes healing after the procedure. When the procedure is heart-related, the vagal stimulation additionally typically (a) reduces mechanical stress by lowering heart rate and pressures, (b) reduces heart rate, and/or (c) improves coronary blood flow.

For some applications, the clinical procedure is selected from one of the following:
- coronary artery bypass graft (CABG) surgery;
- other bypass graft (such as mesocaval shunting and bypass surgery for peripheral blood flow improvement);
- valve replacement surgery;
- heart transplantation;
- other organ transplantation, such as kidney, liver, skin grafting, and bone marrow transplantation;
- percutaneous transluminal coronary angioplasty (PTCA) and/or stenting procedures;
- carotid endarterectomy; and
- abdominal surgery requiring GI tract anastomosis.

In some embodiments of the present invention, the control unit drives the electrode device to apply vagal stimulation, and configures the stimulation to reduce hyperactivity or activity of brain cells, in order to treat conditions such as stroke and Attention Deficit Hyperactivity Disorder (ADHD). In one application, secondary stroke damage to cells in areas adjacent to the hypoxic area is reduced by reducing the cell activity in these areas. In another application, vagal stimulation is configured to help reduce hyperactivity and improve concentration of a subject suffering from ADHD.

In some embodiments of the present invention, the control unit drives the electrode device to apply vagal stimulation, and configures the stimulation to treat one or more of the following conditions by reducing immune system hyperactivation associated with the condition:
- vasculitis, e.g., Wegener granulomatosis, temporal arteritis, Takayasu's arteritis, and/or polyarteritis nodosa;
- systemic sclerosis;
- systemic lupus erythematosus;
- flare of Crohn's disease;
- flare of ulcerative colitis;
- autoimmune hepatitis;
- glomerulonephritis;
- arthritis, e.g., reactive or rheumatoid;
- pancreatitis;
- thyroiditis;
- idiopathic thrombocytopenic purpura (ITP);
- thrombotic thrombocytopenic purpura (TTP);
- multi-organ failure associated with sepsis (especially gram negative sepsis);
- anaphylactic shock;
- Acute Respiratory Distress Syndrome (ARDS);
- asthma;
- an allergy or allergic reaction (such as to a drug or body fluid); and
- multiple sclerosis.

In some embodiments of the present invention, the control unit drives the electrode device to apply vagal stimulation, and configures the stimulation to treat a habitual behavior or a condition associated with a habitual behavior. The inventors hypothesize that vagal stimulation is effective for treating such behavior because the stimulation interferes with acquired habits or routines of the central nervous system (CNS). For some applications, the control unit drives the electrode device to apply the stimulation at non-constant intervals, such as at random, quasi-random (e.g., generated using a random number generator), or seemingly random intervals (e.g., generated using a preselected set or pattern of varying intervals). The use of such variable intervals breaks cycles of the CNS responsible for such habitual behaviors. The use of non-constant intervals typically reduces the likelihood of the CNS cycle becoming synchronized with the stimulation, i.e., reduces the likelihood of accommodation.

Such habitual behaviors or behavior-related conditions include, but are not limited to:
- anorexia, such as anorexia nervosa;
- smoking;
- drug addiction;
- obsessive compulsive disorders;
- sleep apnea, e.g., central sleep apnea;
- Tourette syndrome; and
- hiccups.

In some embodiments of the present invention, the control unit drives the electrode device to apply vagal stimulation that shifts the balance of the autonomic nervous system towards the parasympathetic side thereof, so as to modify the allocation of body resources among different organs and functions. Such vagal stimulation antagonizes the sympathetic system and augments the parasympathetic system, and may be applied in order to treat one or more of the following conditions:
- hyperlipidemia—vagal stimulation is applied to promote lipid metabolism and absorption by the liver, and antagonizes carbohydrate-based sympathetically-derived metabolism;
- insulin resistance (e.g., type II diabetes)—the sympathetic system generally drives muscle tissue to increase its sensitivity to insulin. Vagal stimulation is applied to augment the parasympathetic system, thereby reducing the short-term sensitivity of muscle tissue to insulin. As a result, the long-term insulin sensitivity of muscle tissue increases;
- chronic renal failure—vagal stimulation is applied to increase renal blood flow and glomerular filtration rate (GFR) by reducing blood flow to skeletal muscle (which blood flow is augmented by the sympathetic system), thereby allowing more blood to reach the kidneys, at lower pressures. For some applications, the vagal stimulation is applied while the patient sleeps, or is physically inactive, during which times the need for blood flow to skeletal muscle is reduced. Alternatively or additionally, vagal stimulation increases the GFR by acting on the kidney vascular bed;
- chronic hepatic failure—vagal stimulation is applied to increase blood flow through the portal vein by reducing blood flow to skeletal muscle, thereby increasing blood flow through the liver. As a result, a compromised liver is able to perform additional work, and the condition of the patient improves. For some applications, the vagal stimulation is applied while the patient sleeps, or is physically inactive, during which times the need for blood flow to skeletal muscle is reduced;
- insomnia—vagal stimulation is applied to shift the autonomic balance towards the parasympathetic system, allowing the mind and body to relax. Vagal stimulation promotes activities such as digestion, relaxation, and sleep;
- muscle fatigue (such as associated with heart failure)—vagal stimulation is applied to reduce blood flow and energy consumption of skeletal muscles, thus allowing for muscle rest and recovery (similar to the manner in which beta blockers assist failing hearts);
- muscle hypertonia—vagal stimulation is applied to reduce the tension in skeletal muscles, and/or to reduce the symptoms of hypertonia, such as hypertonia associated with upper motor neuron lesions;
- sexual dysfunction—vagal stimulation is applied to increase the sensitivity of the sexual organs by increasing parasympathetic input, thereby promoting improved sexual function and/or pleasure;

anemia due to reduced production of red blood cells—vagal stimulation is applied to promote increased medullar red blood cell production and/or extramedullary red blood cell production. In unpublished data obtained from chronically vagal stimulated dogs, the inventors have shown increased extramedullary red blood cell production in response to chronic vagal stimulation; and reduced peripheral blood flow—in contrast to the sympathetic system that augments blood flow to skeletal muscle, vagal stimulation reduces blood flow to skeletal muscle, thus augmenting the flow in peripheral blood vessels. In addition, parasympathetic stimulation has a direct effect of vasodilatation on peripheral blood vessels, further augmenting peripheral blood flow.

In some embodiments of the present invention, when applying the signal to the vagus nerve, the control unit drives the electrode device to (a) apply signals to induce the propagation of efferent action potentials towards the heart, and (b) suppress artificially-induced afferent action potentials towards the brain, in order to minimize any unintended side effect of the signal application. When inducing efferent action potentials towards the heart, the control unit typically drives the electrode device to selectively recruit nerve fibers beginning with smaller-diameter fibers, and to recruit progressively larger-diameter fibers as the desired stimulation level increases. Typically, in order to achieve this smaller-to-larger diameter fiber recruitment order, the control unit stimulates myelinated fibers essentially of all diameters using cathodic current from a central cathode, while simultaneously inhibiting fibers in a larger-to-smaller diameter order using anodal current ("efferent anodal current") from a set of one or more anodes placed between the central cathode and the edge of the electrode device closer to the heart ("the efferent anode set"). Thus, for example, if a small anodal current is applied, then action potentials induced by the cathodic current in the larger diameter fibers are inhibited (because the larger diameter fibers are sensitive to even a small anodal current), while action potentials induced by the cathodic current in smaller fibers are allowed to propagate towards the heart. The amount of parasympathetic stimulation delivered to the heart may generally be increased by decreasing the number of fibers affected by the efferent anodal current, in a smaller-to-larger diameter order, e.g., by decreasing the amplitude or frequency of the efferent anodal current applied to the nerve. Alternatively, the cathodic current is increased in order to increase the parasympathetic stimulation.

The control unit typically suppresses afferent action potentials induced by the cathodic current by inhibiting essentially all or a large fraction of fibers using anodal current ("afferent anodal current") from a second set of one or more anodes (the "afferent anode set"). The afferent anode set is typically placed between the central cathode and the edge of the electrode device closer to the brain (the "afferent edge"), to block a large fraction of fibers from conveying signals in the direction of the brain during application of the afferent anodal current.

In some embodiments of the present invention, the cathodic current is applied with an amplitude sufficient to induce action potentials in large- and medium-diameter fibers (e.g., A- and B-fibers), but insufficient to induce action potentials in small-diameter fibers (e.g., C-fibers). Simultaneously, an anodal current is applied in order to inhibit action potentials induced by the cathodic current in the large-diameter fibers (e.g., A-fibers), but not in the small- and medium-diameter fibers (e.g., B- and C-fibers). This combination of cathodic and anodal current generally results in the stimulation of medium-diameter fibers (e.g., B-fibers) only. At the same time, a portion of the afferent action potentials induced by the cathodic current are blocked, as described above. By not stimulating large-diameter fibers, such stimulation generally avoids adverse effects sometimes associated with recruitment of such large fibers, such as dyspnea and hoarseness. Stimulation of small-diameter fibers is avoided because these fibers transmit pain sensations and are important for regulation of reflexes such as respiratory reflexes.

In some embodiments of the present invention, the efferent anode set comprises a plurality of anodes. Application of the efferent anodal current in appropriate ratios from the plurality of anodes in these embodiments generally minimizes the "virtual cathode effect," whereby application of too large an anodal current creates a virtual cathode, which stimulates rather than blocks fibers. When such techniques are not used, the virtual cathode effect generally hinders blocking of smaller-diameter fibers, because a relatively large anodal current is typically necessary to block such fibers, and this same large anodal current induces the virtual cathode effect. Likewise, the afferent anode set typically comprises a plurality of anodes in order to minimize the virtual cathode effect in the direction of the brain.

In some embodiments of the present invention, vagal stimulation is applied in a burst (i.e., a series of pulses). The application of the burst in each cardiac cycle typically commences after a variable delay after a trigger such as a detected R-wave, P-wave, or other feature of an ECG. For some applications, other parameters of the applied burst are also varied in real time. Such other parameters include amplitude, number of pulses per trigger (PPT), pulse duration, and pulse repetition interval (i.e., the interval between the leading edges of two consecutive pulses). For some applications, the delay and/or one or more of the other parameters are calculated in real time using a function, the inputs of which include one or more pre-programmed but updateable constants and one or more sensed parameters, such as the R-R interval between cardiac cycles and/or the P-R interval. Alternatively or additionally, a lookup table of parameters, such as delays and/or other parameters, is used to determine in real time the appropriate parameters for each application of pulses, based on the one or more sensed parameters, and/or based on a predetermined sequence stored in the lookup table. For example, in embodiments of the present invention in which the control unit configures signals applied to the vagus nerve so as to induce cardioversion, such a predetermined sequence may include delays of alternating longer and shorter durations.

The use of the vagal stimulation techniques described herein may also have the additional beneficial effect of preventing electrical remodeling.

"Vagus nerve," and derivatives thereof, as used in the specification and the claims, is to be understood to include portions of the left vagus nerve, the right vagus nerve, and branches of the vagus nerve such as the superior cardiac nerve, superior cardiac branch, and inferior cardiac branch. Similarly, stimulation of the vagus nerve is described herein by way of illustration and not limitation, and it is to be understood that stimulation of other autonomic nerves, including nerves in the epicardial fat pads (SA node and/or AV node fat pads), pulmonary veins, carotid artery, carotid sinus, vena cava vein, and/or internal jugular vein, for treatment of heart conditions or other conditions, is also included within the scope of the present invention.

There is therefore provided, in accordance with an embodiment of the present invention, a treatment method, including:
identifying a subject as one who is selected to undergo an interventional medical procedure; and in response to the identifying, reducing a likelihood of a potential adverse effect of the procedure by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

For some applications, the potential adverse effect includes an immune-mediated response to the procedure, and applying the current includes configuring the current to reduce the likelihood of the immune-mediated response.

In an embodiment, applying the current includes commencing applying the current within the first 7 days after the subject concludes undergoing the procedure. Alternatively, applying the current includes commencing applying the current during the procedure. Further alternatively, applying the current includes commencing applying the current within a three week period that begins one week before the subject begins undergoing the procedure.

In an embodiment, the interventional procedure includes a heart procedure, and identifying the subject includes identifying the subject as one who is selected to undergo the heart procedure. For some applications, applying the current includes configuring the current to reduce mechanical stress of the heart. Alternatively or additionally, applying the current includes configuring the current to reduce a heart rate of the subject. Further alternatively or additionally, applying the current includes configuring the current to improve coronary blood flow of the subject.

In an embodiment, the heart procedure includes coronary bypass surgery, and identifying the subject includes identifying the subject as one who is selected to undergo the coronary bypass surgery. For some applications, applying the current includes configuring the current to reduce a likelihood of postoperative atrial fibrillation. Alternatively or additionally, applying the current includes configuring the current to reduce a likelihood of graft failure. Further alternatively or additionally, applying the current includes configuring the current to reduce a likelihood of a reduction of peripheral blood flow.

In an embodiment, the heart procedure includes carotid endarterectomy, and identifying the subject includes identifying the subject as one who is selected to undergo the carotid endarterectomy. For some applications, applying the current includes configuring the current to reduce a likelihood of restenosis. Alternatively or additionally, applying the current includes configuring the current to reduce a likelihood of intra-operative stroke.

In an embodiment, the interventional procedure includes a surgical procedure, and identifying the subject includes identifying the subject as one who is selected to undergo the surgical procedure. For some applications, the surgical procedure includes a surgical heart procedure, and identifying the subject includes identifying the subject as one who is selected to undergo the surgical heart procedure.

For some applications, the surgical procedure includes an abdominal surgical procedure, and identifying the subject includes identifying the subject as one who is selected to undergo the abdominal surgical procedure. For some applications, applying the current includes configuring the current to reduce a likelihood of a complication selected from the group consisting of: stenosis of gastrointestinal (GI) tract segments involved in the surgical procedure, GI stasis, and flare of inflammatory disease.

In an embodiment, the surgical procedure includes transplantation of tissue selected from the group consisting of: an organ and cells, and identifying the subject includes identifying the subject as one who is selected to undergo the transplantation of the selected tissue.

In an embodiment, the surgical procedure includes implantation of an implantable medical device, and identifying the subject includes identifying the subject as one who is selected to undergo the implantation of the device.

In an embodiment, the surgical procedure includes a heart transplantation procedure, and identifying the subject includes identifying the subject as one who is selected to undergo the heart transplantation procedure. For some applications, applying the current includes applying the current beginning no earlier than 7 days prior to the heart transplantation procedure, and concluding no later than 7 days after the heart transplantation procedure. Alternatively, applying the current includes applying the current beginning at least 2 weeks prior to the heart transplantation procedure. Further alternatively, applying the current includes concluding application of the current at least 2 weeks after the heart transplantation procedure.

In an embodiment, the surgical procedure includes a cardiac procedure selected from the group consisting of: a valve replacement procedure, and a valvoplasty procedure, and identifying the subject includes identifying the subject as one who is selected to undergo the selected cardiac procedure.

In an embodiment, the surgical procedure includes a percutaneous transluminal coronary angioplasty (PTCA) procedure, and identifying the subject includes identifying the subject as one who is selected to undergo the PTCA procedure. For some applications, the potential adverse effect includes restenosis, and reducing the likelihood includes reducing the likelihood of the restenosis.

There is also provided, in accordance with an embodiment of the present invention, a treatment method, including:

determining that a subject suffers from an unwanted habitual behavior;

designating the subject for treatment of the behavior, responsively to the determination; and reducing at least one parameter of the behavior selected from the group consisting of: a rate of occurrence of the behavior, and a level of intensity of the behavior, by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

For some applications, applying the current includes applying the current in response to an indication from the subject that the subject is experiencing a desire to perform the unwanted habitual behavior.

For some applications, applying the current includes applying the current at non-constant intervals. For some applications, applying the current at the non-constant intervals includes applying the current at intervals selected from the group consisting of: random intervals, quasi-random intervals, and seemingly random intervals.

There is further provided, in accordance with an embodiment of the present invention, a treatment method, including:

determining that a subject suffers from an obsessive compulsive disorder;

designating the subject for treatment of the obsessive compulsive disorder, responsively to the determination; and reducing at least one parameter of the disorder selected from the group consisting of: a rate of occurrence of a symptom of the disorder, and a level of intensity of the disorder, by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is still further provided, in accordance with an embodiment of the present invention, a treatment method, including:

determining that a subject smokes;

designating the subject for treatment of the smoking, responsively to the determination; and reducing a rate of occurrence of the smoking by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

For some applications, applying the current includes applying the current in response to an indication from the subject that the subject is experiencing a desire to smoke.

There is yet further provided, in accordance with an embodiment of the present invention, a treatment method, including:

determining that a subject suffers from an addiction to a drug;

designating the subject for treatment of the addiction, responsively to the determination; and reducing at least one parameter of the addiction selected from the group consisting of: a rate of occurrence of use of the drug, and a level of intensity of use of the drug, by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

For some applications, the drug includes nicotine, and determining includes determining that the subject suffers from the addiction to nicotine.

For some applications, applying the current includes applying the current in response to an indication from the subject that the subject is experiencing a desire to administer the drug.

There is additionally provided, in accordance with an embodiment of the present invention, a treatment method, including:

determining that a subject suffers from Tourette syndrome;

designating the subject for treatment of the syndrome, responsively to the determination; and reducing at least one parameter of the syndrome selected from the group consisting of: a rate of occurrence of the syndrome, and a level of intensity of a symptom of the syndrome, by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is yet additionally provided, in accordance with an embodiment of the present invention, a treatment method, including:

determining that a subject suffers from a sleep disorder;

designating the subject for treatment of the sleep disorder, responsively to the determination; and reducing at least one parameter of the disorder selected from the group consisting of: a rate of occurrence of the disorder, and a level of intensity of the disorder, by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

In an embodiment, the sleep disorder includes sleep apnea, and determining includes determining that the subject suffers from the sleep apnea.

In an embodiment, the sleep disorder includes insomnia, and determining includes determining that the subject suffers from the insomnia, and applying the current includes configuring the current to improve at least one parameter of sleep of the subject selected from the group consisting of: quality of sleep, and duration of sleep. For some applications, applying the current includes applying the current in response to an indication from the subject that the subject is experiencing difficulty sleeping.

There is still additionally provided, in accordance with an embodiment of the present invention, a treatment method, including:

determining that a subject suffers from insulin resistance;

designating the subject for treatment of the insulin resistance, responsively to the determination; and reducing the insulin resistance by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

For some applications, applying the current includes configuring the current to reduce short-term sensitivity of muscle tissue to insulin.

There is further provided, in accordance with an embodiment of the present invention, a treatment method, including:

determining that a subject suffers from renal failure;

designating the subject for treatment of the renal failure, responsively to the determination; and improving renal function of the subject by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

For some applications, applying the current includes configuring the current to increase a glomerular filtration rate (GFR) of the subject by acting on a kidney vascular bed.

For some applications, applying the current includes configuring the current to reduce blood flow to skeletal muscle of the subject. For some applications, applying the current includes applying the current during a period of time selected from the group consisting of: a period when the subject is sleeping, and a period during which the subject is physically inactive.

For some applications, the method includes receiving a signal from the subject signifying that the subject is undergoing dialysis, and applying the current includes applying the current responsively to the received signal.

There is still further provided, in accordance with an embodiment of the present invention, a treatment method, including:

determining that a subject suffers from hepatic failure;

designating the subject for treatment of the hepatic failure, responsively to the determination; and improving hepatic function of the subject by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

For some applications, applying the current includes configuring the current to increase blood flow through a portal vein of the subject by reducing blood flow to skeletal muscle.

For some applications, applying the current includes applying the current during a period of time selected from the group consisting of: a period when the subject is sleeping, and a period during which the subject is physically inactive.

There is additionally provided, in accordance with an embodiment of the present invention, a treatment method, including:

determining that a subject suffers from a symptom of muscle fatigue;

designating the subject for treatment of the muscle fatigue, responsively to the determination; and reducing a level of severity of the symptom of muscle fatigue by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is yet additionally provided, in accordance with an embodiment of the present invention, a treatment method, including:

determining that a subject suffers from at least one condition selected from the group consisting of: impaired sexual function, and impaired sexual pleasure;

designating the subject for treatment of the condition, responsively to the determination; and improving the condition by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is still additionally provided, in accordance with an embodiment of the present invention, a treatment method, including:

determining that a subject suffers from anemia;

designating the subject for treatment of the anemia, responsively to the determination; and promoting red blood cell production by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is also provided, in accordance with an embodiment of the present invention, a treatment method, including:

determining that a subject suffers from reduced peripheral blood flow;

designating the subject for treatment of the reduced peripheral blood flow, responsively to the determination; and applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is further provided, in accordance with an embodiment of the present invention, a treatment method, including:

determining that a subject has suffered a cerebrovascular accident (CVA);

designating the subject for treatment of the CVA, responsively to the determination; and reducing a level of damage due to the CVA by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is still further provided, in accordance with an embodiment of the present invention, a treatment method, including:

determining that a subject suffers from Attention Deficit Hyperactivity Disorder (ADHD);

designating the subject for treatment of the ADHD, responsively to the determination; and reducing at least one symptom of the ADHD by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

For some applications, applying the current includes configuring the current to reduce the symptom by reducing hyperactivity or activity of brain cells of the subject.

There is yet further provided, in accordance with an embodiment of the present invention, a treatment method, including:

determining that a subject has suffered a stroke;

designating the subject for treatment of the stroke, responsively to the determination; and treating the stroke by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject.

For some applications, applying the current includes configuring the current to treat the stroke by reducing hyperactivity or activity of brain cells of the subject.

For some applications, applying the current includes configuring the current to reduce secondary stroke damage to cells in areas adjacent to a hypoxic area by reducing cell activity in the areas. Alternatively or additionally, applying the current includes configuring the current to reduce the likelihood of an immune-mediated response to the stroke.

There is also provided, in accordance with an embodiment of the present invention, a treatment method, including:

determining that a subject suffers from a condition selected from the group consisting of: an allergy, an allergic reaction, and multiple sclerosis;

designating the subject for treatment of the selected condition, responsively to the determination; and reducing at least one symptom of the condition by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is additionally provided, in accordance with an embodiment of the present invention, a treatment method, including:

determining that a subject suffers from a condition selected from the group consisting of: vasculitis, Wegener granulomatosis, temporal arteritis, Takayasu arteritis, polyarteritis nodosa, systemic sclerosis, systemic lupus erythematosus, flare of Crohn's disease, flare of ulcerative colitis, autoimmune hepatitis, glomerulonephritis, arthritis, reactive arthritis, rheumatoid arthritis, pancreatitis, thyroiditis, idiopathic thrombocytopenic purpura (ITP), thrombotic thrombocytopenic purpura (TTP), multi-organ failure associated with sepsis, anaphylactic shock, Acute Respiratory Distress Syndrome (ARDS), and asthma;

designating the subject for treatment of the selected condition, responsively to the determination; and reducing immune system hyperactivation associated with the selected condition by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

There is yet additionally provided, in accordance with an embodiment of the present invention, a treatment method, including:

determining that a subject suffers from a condition;

designating the subject for treatment of the condition by regulation of cell division of the subject, responsively to the determination; and treating the condition by regulating the cell division of the subject by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject.

In an embodiment, applying the current includes configuring the current to increase cell division of the subject. For example, the condition may be associated with improperly-regulated cell division, and determining may include determining that the subject suffers from the condition associated with improperly-regulated cell division. Alternatively or additionally, the condition is selected from the group consisting of: anemia, a neurodegenerative disease, liver cirrhosis, an immune deficiency, a skin burn, a skin abrasion, a muscle degenerative disorder, cardiac failure, and a reproductive system disorder, and determining includes determining that the subject suffers from the selected condition.

In an embodiment, applying the current includes configuring the current to decrease cell division of the subject. For some applications, the condition is selected from the group consisting of: a neoplastic disorder, a hematologic malignancy, and polycythemia vera, and determining includes determining that the subject suffers from the selected condition.

There is still additionally provided, in accordance with an embodiment of the present invention, a treatment method, including:

determining that a subject suffers from hiccups;

designating the subject for treatment of the hiccups, responsively to the determination; and reducing at least one parameter of the hiccups selected from the group consisting of: a rate of occurrence of the hiccups, and a level of intensity of the hiccups, by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, and a right ventricle of the subject.

There is yet additionally provided, in accordance with an embodiment of the present invention, apparatus for treating a subject, including:

an electrode device, adapted to be coupled to a parasympathetic site of the subject selected from the group consisting: of a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject; and a control unit, adapted to:

drive the electrode device to apply a current to the site, receive a sensed physiological value of the subject selected from the group consisting of: a temperature of the subject, a blood glucose level of the subject, a blood lipid level of the subject, a blood lactic acid level of the subject, a blood $CO_2$ level of the subject, a blood $O_2$ level of the subject, a blood urea level of the subject, a blood creatinine level of the subject, and a blood ammonia level of the subject, and set at least one parameter of the applied current responsively to the sensed physiological value.

For some applications, the control unit is adapted to configure the applied current to reduce a heart rate of the subject.

There is still additionally provided, in accordance with an embodiment of the present invention, a method for treating a subject, including:

applying a current to a parasympathetic site of the subject selected from the group consisting: of a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject;

receiving a sensed physiological value of the subject selected from the group consisting of: a temperature of the subject, a blood glucose level of the subject, a blood lipid level of the subject, a blood lactic acid level of the subject, a blood $CO_2$ level of the subject, a blood $O_2$ level of the subject, a blood urea level of the subject, a blood creatinine level of the subject, and a blood ammonia level of the subject; and setting at least one parameter of the applied current responsively to the sensed physiological value.

There is yet additionally provided, in accordance with an embodiment of the present invention, apparatus including an electrode assembly adapted to be coupled to nervous tissue of a subject, the electrode assembly including one or more conductive elements, and at least a portion of the electrode assembly is adapted to be dissolvable after the electrode assembly has been coupled to the tissue.

In an embodiment, the nervous tissue includes a nerve of the subject, and the electrode assembly is adapted to be coupled to the nerve.

In an embodiment, the electrode assembly is adapted to come loose from the tissue upon dissolving of the dissolvable at least a portion thereof.

For some applications, the dissolvable at least a portion of the electrode assembly includes a material selected from the group consisting of: polyglycolic acid (PGA), and poly(L-lactide) acid (PLL).

For some applications, when the electrode assembly is coupled to the tissue, a portion of the electrode assembly is positioned within 2 cm of the tissue, and the portion does not include any metal components. For some applications, the electrode assembly includes electrode leads including metal wires, and the electrode assembly is configured such that the metal wires are not positioned within 2 cm of the tissue when the electrode assembly is coupled to the tissue.

In an embodiment, the electrode assembly includes electrode leads, and when the electrode assembly is coupled to the tissue, at least a portion of the electrode leads are positioned within 2 cm of the tissue, and the portion of the electrode leads includes tubes including an electrically conductive biologically-compatible liquid.

For some applications, the apparatus includes a control unit, adapted to measure an impedance of the electrode assembly, and to determine, responsively to the measured impedance, whether the dissolvable at least a portion of the electrode assembly has dissolved sufficiently to enable safe removal of the electrode assembly from the subject.

There is also provided, in accordance with an embodiment of the present invention, a method including coupling an electrode assembly to nervous tissue of a subject, the electrode assembly including one or more conductive elements, and at least a portion of the electrode assembly is adapted to be dissolvable after the electrode assembly has been coupled to the tissue.

For some applications, the method includes removing a non-dissolvable portion of the electrode assembly from the tissue upon dissolving of the dissolvable at least a portion thereof.

The present invention will be more fully understood from the following detailed description of embodiments thereof, taken together with the drawings, in which:

BRIEF DESCRIPTION OF THE DRAWINGS

FIG. 2C is a simplified perspective illustration of the electrode device of FIG. 2A, in accordance with an embodiment of the present invention;

DETAILED DESCRIPTION OF EMBODIMENTS

Figure 1:
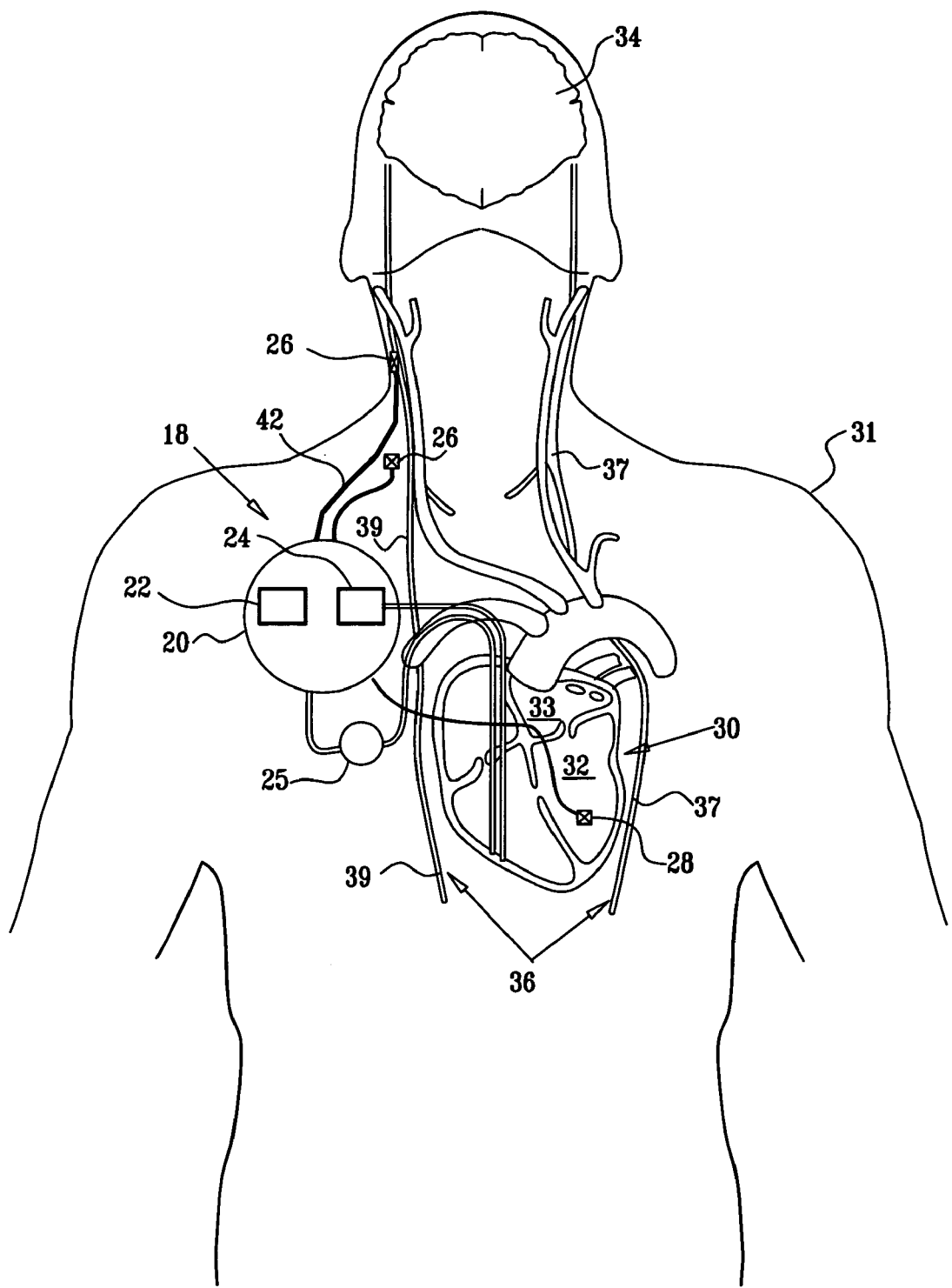
FIG. 1 is a block diagram that schematically illustrates a vagal stimulation system applied to a vagus nerve of a subject, in accordance with an embodiment of the present invention.

FIG. 1 is a block diagram that schematically illustrates a vagal stimulation system 18 comprising a multipolar electrode device 26, in accordance with an embodiment of the present invention. Electrode device 26 is applied to a portion of a vagus nerve 36 (a left vagus nerve 37 and/or a right vagus nerve 39), which innervates a heart 30 of a subject 31. Alternatively, electrode device 26 is applied to an epicardial fat pad, a pulmonary vein, a carotid artery, a carotid sinus, a coronary sinus, a vena cava vein, a right ventricle, or a jugular vein (configurations not shown). Typically, system 18 is utilized for treating a heart condition such as heart failure and/or cardiac arrhythmia. Vagal stimulation system 18 further comprises an implanted or external control unit 20, which typically communicates with electrode device 26 over a set of leads 42. Typically, control unit 20 drives electrode device 26 to (i) apply signals to induce the propagation of efferent nerve impulses towards heart 30, and (ii) suppress artificially-induced afferent nerve impulses towards a brain 34 of the subject, in order to minimize unintended side effects of the signal application. The efferent nerve pulses in vagus nerve 36 are typically induced by electrode device 26 in order to regulate the heart rate of the subject.

For some applications, control unit 20 is adapted to receive feedback from one or more of the electrodes in electrode device 26, and to regulate the signals applied to the electrode device responsive thereto.

Control unit 20 is typically adapted to receive and analyze one or more sensed physiological parameters or other parameters of the subject, such as heart rate, electrocardiogram (ECG), blood pressure, indicators of decreased cardiac contractility, cardiac output, norepinephrine concentration, left ventricular end diastolic pressure (LVEDP), or motion of the subject. In order to receive these sensed parameters, control unit 20 may comprise, for example, an ECG monitor 24, connected to a site on the subject's body such as heart 30, for example using one or more subcutaneous sensors or ventricular and/or atrial intracardiac sensors. The control unit may also comprise an accelerometer 22 for detecting motion of the subject. Alternatively, ECG monitor 24 and/or accelerometer 22 comprise separate implanted devices placed external to control unit 20, and, optionally, external to the subject's body. Alternatively or additionally, control unit 20 receives signals from one or more physiological sensors 28, such as blood pressure sensors. Sensors 28 are typically implanted in the subject, for example in a left ventricle 32 of heart 30. For example, sensors 28 may comprise a pressure gauge for measuring LVEDP, which gauge may be adapted to be placed in left ventricle 32, a left atrium 33 of heart 30, or in a pulmonary artery.

Figure 2A:
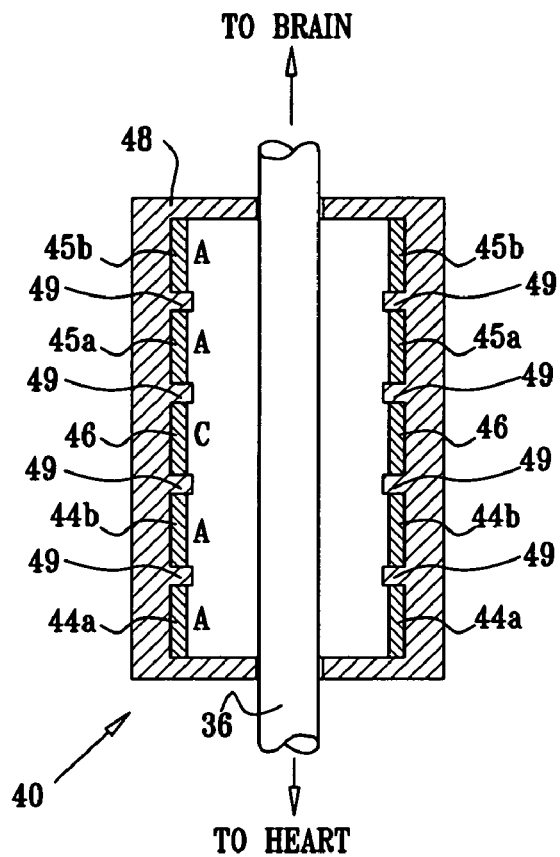
FIG. 2A is a simplified cross-sectional illustration of a multipolar electrode device applied to a vagus nerve, in accordance with an embodiment of the present invention.

FIG. 2A is a simplified cross-sectional illustration of a generally-cylindrical electrode device 40 applied to vagus nerve 36, in accordance with an embodiment of the present invention. For some applications, electrode device 26 (FIG. 1) comprises electrode device 40. Alternatively, electrode device 26 comprises an electrode device known in the art of nerve stimulation, such as those described in some of the references incorporated herein by reference. Electrode device 40 comprises a central cathode 46 for applying a negative current ("cathodic current") in order to stimulate vagus nerve 36, as described below. Electrode device 40 additionally comprises a set of one or more anodes 44 (44a, 44b, herein: "efferent anode set 44"), placed between cathode 46 and the edge of electrode device 40 closer to heart 30 (the "efferent edge"). Efferent anode set 44 applies a positive current ("efferent anodal current") to vagus nerve 36, for blocking action potential conduction in vagus nerve 36 induced by the cathodic current, as described below. Typically, electrode device 40 comprises an additional set of one or more anodes 45 (45a, 45b, herein: "afferent anode set 45"), placed between cathode 46 and the edge of electrode device 40 closer to brain 34. Afferent anode set 45 applies a positive current ("afferent anodal current") to vagus nerve 36, in order to block propagation of action potentials in the direction of the brain during application of the cathodic current.

For some applications, the one or more anodes of efferent anode set 44 are directly electrically coupled to the one or more anodes of afferent anode set 45, such as by a common wire or shorted wires providing current to both anode sets substantially without any intermediary elements. Typically, coatings on the anodes, shapes of the anodes, positions of the anodes, sizes of the anodes and/or distances of the various anodes from the nerve are regulated so as to produce desired ratios of currents and/or desired activation functions delivered through or caused by the various anodes. For example, by varying one or more of these characteristics, the relative impedance between the respective anodes and central cathode 46 is regulated, whereupon more anodal current is driven through the one or more anodes having lower relative impedance. In these applications, central cathode 46 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Figure 2B:
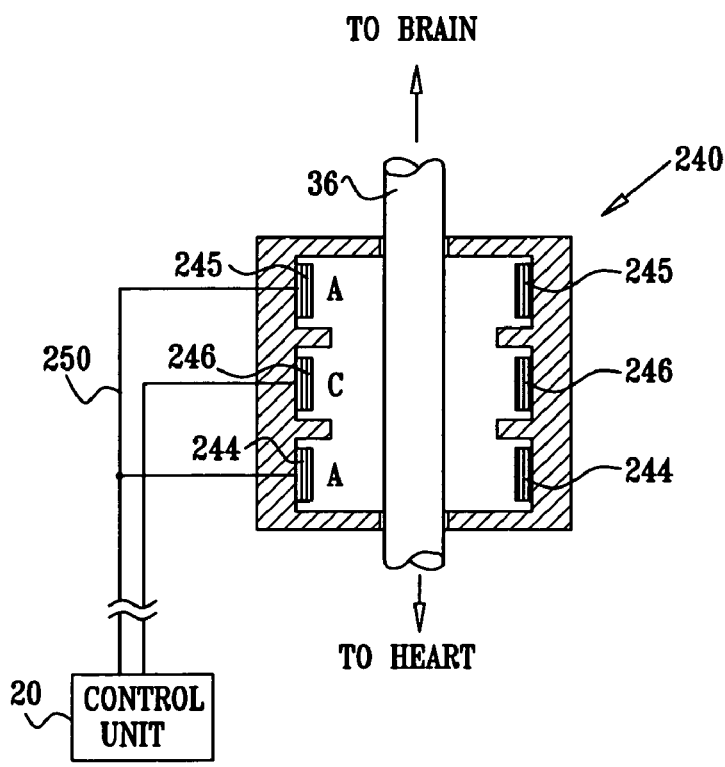
FIG. 2B is a simplified cross-sectional illustration of a generally-cylindrical electrode device applied to a vagus nerve, in accordance with an embodiment of the present invention.

Reference is now made to FIG. 2B, which is a simplified cross-sectional illustration of a generally-cylindrical electrode device 240 applied to vagus nerve 36, in accordance with an embodiment of the present invention. Electrode device 240 comprises exactly one efferent anode 244 and exactly one afferent anode 245, which are electrically coupled to each other, such as by a common wire 250 or shorted wires providing current to both anodes 244 and 245, substantially without any intermediary elements. The cathodic current is applied by a cathode 246 with an amplitude sufficient to induce action potentials in large- and medium-diameter fibers (e.g., A- and B-fibers), but insufficient to induce action potentials in small-diameter fibers (e.g., C-fibers).

Reference is again made to FIG. 2A. Cathodes 46 and anode sets 44 and 45 (collectively, "electrodes") are typically mounted in an electrically-insulating cuff 48 and separated from one another by insulating elements such as protrusions 49 of the cuff. Typically, the width of the electrodes is between about 0.5 and about 2 millimeters, or is equal to approximately one-half the radius of the vagus nerve. The electrodes are typically recessed so as not to come in direct contact with vagus nerve 36. For some applications, such recessing enables the electrodes to achieve generally uniform field distributions of the generated currents and/or generally uniform values of the activation function defined by the electric potential field in the vicinity of vagus nerve 24. Alternatively or additionally, protrusions 49 allow vagus nerve 24 to swell into the canals defined by the protrusions, while still holding the vagus nerve centered within cuff 48 and maintaining a rigid electrode geometry. For some applications, cuff 48 comprises additional recesses separated by protrusions, which recesses do not contain active electrodes. Such additional recesses accommodate swelling of vagus nerve 24 without increasing the contact area between the vagus nerve and the electrodes.

For some applications, the distance between the electrodes and the axis of the vagus nerve is between about 1 and about 4 millimeters, and is greater than the closest distance from the ends of the protrusions to the axis of the vagus nerve. Typically, protrusions 49 are relatively short (as shown). For some applications, the distance between the ends of protrusions 49 and the center of the vagus nerve is between about 1 and 3 millimeters. (Generally, the diameter of the vagus nerve is between about 2 and 3 millimeters.) Alternatively, for some applications, protrusions 49 are longer and/or the electrodes are placed closer to the vagus nerve in order to reduce the energy consumption of electrode device 40.

In an embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from a plurality of anodes generally minimizes the "virtual cathode effect," whereby application of too large an anodal current stimulates rather than blocks fibers. In an embodiment, anode 44a applies a current with an amplitude equal to about 0.5 to about 5 milliamps (typically one-third of the amplitude of the current applied by anode 44b). When such techniques are not used, the virtual cathode effect generally hinders blocking of smaller-diameter fibers, as described below, because a relatively large anodal current is generally necessary to block such fibers.

Anode 44a is typically positioned in cuff 48 to apply current at the location on vagus nerve 36 where the virtual cathode effect is maximally generated by anode 44b. For applications in which the blocking current through anode 44b is expected to vary substantially, efferent anode set 44 typically comprises a plurality of virtual-cathode-inhibiting anodes 44a, one or more of which is activated at any time based on the expected magnitude and location of the virtual cathode effect.

Likewise, afferent anode set 45 typically comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

FIG. 2C is a simplified perspective illustration of electrode device 40 (FIG. 2A), in accordance with an embodiment of the present invention. When applied to vagus nerve 36, electrode device 40 typically encompasses the nerve. As described, control unit 20 typically drives electrode device 40 to (i) apply signals to vagus nerve 36 in order to induce the propagation of efferent action potentials towards heart 30, and (ii) suppress artificially-induced afferent action potentials towards brain 34. The electrodes typically comprise ring electrodes adapted to apply a generally uniform current around the circumference of the nerve, as best shown in FIG. 2C.

Alternatively, ordinary, non-cuff electrodes are used, such as when the electrodes are placed on the epicardial fat pads instead of on the vagus nerve.

In an embodiment of the present invention, a method for surgically implanting electrode device 26 comprises: (a) placing the electrode device around vagus nerve 36, (b) during the implantation procedure, introducing saline solution into the electrode device such that the solution is in contact with both the electrodes and the nerve, and (c) measuring an inter-electrode impedance during the implantation procedure. Such an impedance measurement enables the surgeon to determine during the procedure (a) whether the electrodes are positioned appropriately, (b) whether sufficient saline solution has been introduced into and remained in electrode device 26, (c) whether the electrodes are the correct size for the nerve, and (d) whether the electrodes are in good contact with the nerve. Expected values for the impedance measurement, and their typical interpretations, include:

- a low value, such as between about 100 and about 300 ohms, which typically occurs if the electrodes are in poor contact with the nerve, such as because the diameter of the electrode is larger than that of the nerve. When there is such poor contact, the electrodes are short-circuited by the saline solution, resulting in the low impedance;
- a high value, such as greater than about 1000 ohms, which typically occurs if electrode device 26 is not filled properly with saline solution, which causes a disconnect between the electrodes and the nerve; or
- a medium value, such as between about 300 and about 1000 ohms, which indicates that the electrodes are in good contact with the nerve, so that most of the current travels through the nerve.

If the impedance differs from an expected value, the surgeon corrects the placement by, for example, repositioning the electrode device, removing the electrode device and implanting another electrode device having a different size, and/or introducing additional saline solution into the electrode device. The techniques of this embodiment are also applicable to implanting electrode devices on a body tissue other than the vagus nerve.

Figure 3:
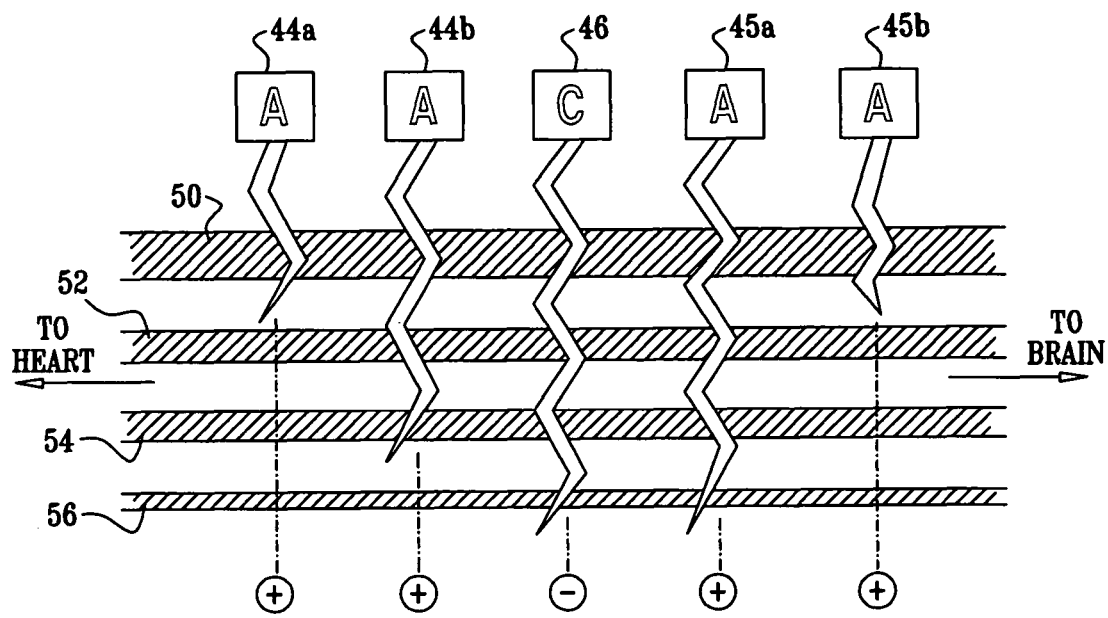
FIG. 3 is a conceptual illustration of the application of current to a vagus nerve, in accordance with an embodiment of the present invention.

FIG. 3 is a conceptual illustration of the application of current to vagus nerve 36 in order to achieve smaller-to-larger diameter fiber recruitment, in accordance with an embodiment of the present invention. When inducing efferent action potentials towards heart 30, control unit 20 drives electrode device 40 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Typically, in order to achieve this recruitment order, the control unit stimulates myelinated fibers essentially of all diameters using cathodic current from cathode 46, while simultaneously inhibiting fibers in a larger-to-smaller diameter order using efferent anodal current from efferent anode set 44. For example, FIG. 3 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 30. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. Alternatively or additionally, in order to increase the number of fibers stimulated, while simultaneously decreasing the average diameter of fibers stimulated, the amplitudes of the currents applied by cathode 46 and efferent anode set 44 are both increased (thereby increasing both the number of fibers stimulated and blocked). In addition, for any given number of fibers stimulated (and not blocked), the amount of stimulation delivered to the heart can be increased by increasing the PPT, frequency, and/or pulse width of the current applied to vagus nerve 36.

In order to suppress artificially-induced afferent action potentials from traveling towards the brain in response to the cathodic stimulation, control unit 20 typically drives electrode device 40 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In an embodiment of the present invention, the amplitude of the cathodic current applied in the vicinity of the vagus nerve is between about 2 milliamps and about 10 milliamps. Such a current is typically used in embodiments that employ techniques for achieving generally uniform stimulation of the vagus nerve, i.e., stimulation in which the stimulation applied to fibers on or near the surface of the vagus nerve is generally no more than about 400% greater than stimulation applied to fibers situated more deeply in the nerve. This corresponds to stimulation in which the value of the activation function at fibers on or near the surface of the vagus nerve is generally no more than about four times greater than the value of the activation function at fibers situated more deeply in the nerve. For example, as described hereinabove with reference to FIG. 2A, the electrodes may be recessed so as not to come in direct contact with vagus nerve 24, in order to achieve generally uniform values of the activation function. Typically, but not necessarily, embodiments using approximately 5 mA of cathodic current have the various electrodes disposed approximately 0.5 to 2.5 mm from the axis of the vagus nerve. Alternatively, larger cathodic currents (e.g., 10-30 mA) are used in combination with electrode distances from the axis of the vagus nerve of greater than 2.5 mm (e.g., 2.5-4.0 mm), so as to achieve an even greater level of uniformity of stimulation of fibers in the vagus nerve.

In an embodiment of the present invention, the cathodic current is applied by cathode 46 with an amplitude sufficient to induce action potentials in large- and medium-diameter fibers 50, 52, and 54 (e.g., A- and B-fibers), but insufficient to induce action potentials in small-diameter fibers 56 (e.g., C-fibers). Simultaneously, an anodal current is applied by anode 44b in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked by anode 45a, as described above. Alternatively, the afferent anodal current is configured to not fully block afferent action potentials, or is simply not applied. In these cases, artificial afferent action potentials are nevertheless generally not generated in C-fibers, because the applied cathodic current is not strong enough to generate action potentials in these fibers.

These techniques for efferent stimulation of only B-fibers are typically used in combination with techniques described hereinabove for achieving generally uniform stimulation of the vagus nerve. Such generally uniform stimulation enables the use of a cathodic current sufficiently weak to avoid stimulation of C-fibers near the surface of the nerve, while still sufficiently strong to stimulate B-fibers, including B-fibers situated more deeply in the nerve, i.e., near the center of the nerve. For some applications, when employing such techniques for achieving generally uniform stimulation of the vagus nerve, the amplitude of the cathodic current applied by cathode 46 may be between about 3 and about 10 milliamps, and the amplitude of the anodal current applied by anode 44b may be between about 1 and about 7 milliamps. (Current applied at a different site and/or a different time is used to achieve a net current injection of zero.)

In an embodiment of the present invention, stimulation of the vagus nerve is applied responsive to one or more sensed parameters. Control unit 20 is typically configured to commence or halt stimulation, or to vary the amount and/or timing of stimulation in order to achieve a desired target heart rate, typically based on configuration values and on parameters including one or more of the following:

Heart rate—the control unit can be configured to drive electrode device 26 to stimulate the vagus nerve only when the heart rate exceeds a certain value.

ECG readings—the control unit can be configured to drive electrode device 26 to stimulate the vagus nerve based on certain ECG readings, such as readings indicative of designated forms of arrhythmia. Additionally, ECG readings are typically used for achieving a desire heart rate, as described below with reference to FIG. 4.

Blood pressure—the control unit can be configured to regulate the current applied by electrode device 26 to the vagus nerve when blood pressure exceeds a certain threshold or falls below a certain threshold.

Indicators of decreased cardiac contractility—these indicators include left ventricular pressure (LVP). When LVP and/or d(LVP)/dt exceeds a certain threshold or falls below a certain threshold, control unit 20 can drive electrode device 26 to regulate the current applied by electrode device 26 to the vagus nerve.

Motion of the subject—the control unit can be configured to interpret motion of the subject as an indicator of increased exertion by the subject, and appropriately reduce parasympathetic stimulation of the heart in order to allow the heart to naturally increase its rate.

Heart rate variability—the control unit can be configured to drive electrode device 26 to stimulate the vagus nerve based on heart rate variability, which is typically calculated based on certain ECG readings.

Norepinephrine concentration—the control unit can be configured to drive electrode device 26 to stimulate the vagus nerve based on norepinephrine concentration.

Cardiac output—the control unit can be configured to drive electrode device 26 to stimulate the vagus nerve based on cardiac output, which is typically determined using impedance cardiography.

Baroreflex sensitivity—the control unit can be configured to drive electrode device 26 to stimulate the vagus nerve based on baroreflex sensitivity.

LVEDP—the control unit can be configured to drive electrode device 26 to stimulate the vagus nerve based on LVEDP, which is typically determined using a pressure gauge, as described hereinabove with reference to FIG. 1.

The parameters and behaviors included in this list are for illustrative purposes only, and other possible parameters and/or behaviors will readily present themselves to those skilled in the art, having read the disclosure of the present patent application.

In an embodiment of the present invention, control unit 20 is configured to drive electrode device 26 to stimulate the vagus nerve so as to reduce the heart rate of the subject towards a target heart rate. The target heart rate is typically (a) programmable or configurable, (b) determined responsive to one or more sensed physiological values, such as those described hereinabove (e.g., motion, blood pressure, etc.), and/or (c) determined responsive to a time of day or circadian cycle of the subject. Parameters of stimulation are varied in real time in order to vary the heart-rate-lowering effects of the stimulation. For example, such parameters may include the amplitude of the applied current. Alternatively or additionally, in an embodiment of the present invention, the stimulation is applied in bursts (i.e., series of pulses), which are synchronized or are not synchronized with the cardiac cycle of the subject, such as described hereinbelow with reference to FIG. 4. Parameters of such bursts typically include, but are not limited to:

Timing of the stimulation within the cardiac cycle. Delivery of each of the bursts typically begins after a fixed or variable delay following an ECG feature, such as each R- or P-wave. For some applications, the delay is between about 20 ms and about 300 ms from the R-wave, or between about 100 and about 500 ms from the P-wave.

Pulse duration (width). Longer pulse durations typically result in a greater heart-rate-lowering effect. For some applications, the pulse duration is between about 0.2 and about 4 ms.

Pulse repetition interval within each burst. Maintaining a pulse repetition interval (the time from the initiation of a pulse to the initiation of the following pulse within the same burst) greater than about 3 ms generally results in maximal stimulation effectiveness for multiple pulses within a burst. For some applications, the pulse repetition interval is between about 3 and about 10 ms.

Pulses per trigger (PPT). A greater PPT (the number of pulses in each burst after a trigger such as an R-wave) typically results in a greater heart-rate-lowering effect. For some applications, PPT is between about 0 and about 8. For some applications, PPT is varied while pulse repetition interval is kept constant.

Amplitude. A greater amplitude of the signal applied typically results in a greater heart-rate-lowering effect. The amplitude is typically less than about 10 milliamps, e.g., between about 2 and about 10 milliamps. For some applications, the amplitude is between about 2 and about 6 milliamps.

Duty cycle (number of bursts per heart beat). Application of stimulation every heartbeat (i.e., with a duty cycle of 1) typically results in a greater heart-rate-lowering effect. For less heart rate reduction, stimulation is applied less frequently than every heartbeat (e.g., duty cycle=60%-90%), or only once every several heartbeats (e.g., duty cycle=5%-40%).

Choice of vagus nerve. Stimulation of the right vagus nerve typically results in greater heart rate reduction than stimulation of the left vagus nerve.

"On"/"off" ratio and timing. For some applications, the device operates intermittently, alternating between "on" and "off" states, the length of each state typically being between 0 and about 1 day, such as between 0 and about 300 seconds (with a 0-length "off" state equivalent to always "on"). No stimulation is applied during the "off" state. Greater heart rate reduction is typically achieved if the device is "on" a greater portion of the time.

For some applications, values of one or more of the parameters are determined in real time using feedback (i.e., responsive to one or more inputs). The inputs typically include sensed physiological values, such as:
   a temperature of the subject;
   a blood glucose level of the subject;
   a blood lipid level of the subject;
   a blood lactic acid level of the subject;
   a blood $CO_2$ or $O_2$ level of the subject; and/or
   a blood urea, creatinine, or ammonia level of the subject.

For some applications, values of one or more of the parameters are set responsively to one or more inputs. The inputs may include, for example, a signal generated by the subject, such as by applying a magnet, or sending a wireless command to change a parameter value. For some applications, the patient sends such a signal to signify:
   a convenient or inconvenient time for stimulation;
   that the patient is taking a drug;
   that the patient is undergoing dialysis;
   that the patient is performing exercise;
   that the patient is going to sleep or awakening; and/or
   that the patient is experiencing a subjective feeling of a habitual need.

For some applications, an intermittency ("on"/"off") parameter is determined in real time using such feedback. The inputs used for such feedback typically include one or more of the following: (a) motion or activity of the subject (e.g., detected using an accelerometer), (b) the average heart rate of the subject, (c) the average heart rate of the subject when the device is in "off" mode, (d) the average heart rate of the subject when the device is in "on" mode, and/or (e) the time of day. The average heart rate is typically calculated over a period of at least about 10 seconds. For some applications, the average heart rate during an "on" or "off" period is calculated over the entire "on" or "off" period. For example, the device may operate in continuous "on" mode when the subject is exercising and therefore has a high heart rate, and the device may alternate between "on" and "off" when the subject is at rest. As a result, the heart-rate-lowering effect is concentrated during periods of high heart rate, and the nerve is allowed to rest when the heart rate is generally naturally lower. For some applications, the device determines the ratio of "on" to "off" durations, the duration of the "on" periods, and/or the durations of the "off" periods using feedback. Optionally, the device determines the "on"/"off" parameter in real time using the integral feedback techniques described hereinbelow, and/or other feedback techniques described hereinbelow, mutatis mutandis.

For some applications, heart rate regulation is achieved by setting two or more parameters in combination. For example, if it is desired to apply 5.2 pulses of stimulation, the control unit may apply 5 pulses of 1 ms duration each, followed by a single pulse of 0.2 ms duration. For other applications, the control unit switches between two values of PPT, so that the desired PPT is achieved by averaging the applied PPTs. For example, a sequence of PPTs may be 5, 5, 5, 5, 6, 5, 5, 5, 5, 6, . . . , in order to achieve an effective PPT of 5.2.

In an embodiment of the present invention, the heart rate regulation algorithm is implemented using only integer arithmetic. For example, division is implemented as integer division by a power of two, and multiplication is always of two 8-bit numbers. For some applications, time is measured in units of $1/128$ of a second.

In an embodiment of the present invention, control unit 20 implements an integral feedback controller, which can most generally be described by:

$$K = K_I * \int e\, dt$$

in which K represents the strength of the feedback, $K_I$ is a coefficient, and $\int e\, dt$ represents the cumulative error. It is to be understood that such an integral feedback controller can be implemented in hardware, or in software running in control unit 20.

In an embodiment of such an integral controller, heart rate is typically expressed as an R-R interval (the inverse of heart rate). Parameters of the integral controller typically include TargetRR (the target R-R interval) and TimeCoeff (which determines the overall feedback reaction time).

Typically, following the detection of each R-wave, the previous R-R interval is calculated and assigned to a variable (LastRR). e (i.e., the difference between the target R-R interval and the last measured R-R interval) is then calculated as:

$$e = \text{Target}RR - \text{Last}RR$$

e is typically limited by control unit 20 to a certain range, such as between −0.25 and +0.25 seconds, by reducing values outside the range to the endpoint values of the range. Similarly, LastRR is typically limited, such as to 255/128 seconds. The error is then calculated by multiplying LastRR by e:

$$\text{Error} = e * \text{Last}RR$$

A cumulative error (representing the integral in the above generalized equation) is then calculated by dividing the error by TimeCoeff and adding the result to the cumulative error, as follows:

$$Integral = Integral + Error/2^{TimeCoeff}$$

The integral is limited to positive values less than, e.g., 36,863. The number of pulses applied in the next series of pulses (pulses per trigger, or PPT) is equal to the integral/4096.

The following table illustrates example calculations using a heart rate regulation algorithm that implements an integral controller, in accordance with an embodiment of the present invention. In this example, the parameter TargetRR (the target heart rate) is set to 1 second (128/128 seconds), and the parameter TimeCoeff is set to 0. The initial value of Integral is 0. As can be seen in the table, the number of pulses per trigger (PPT) increases from 0 during the first heart beat, to 2 during the fourth heart beat of the example.

|  | Heart Beat Number | | | |
| --- | --- | --- | --- | --- |
|  | 1 | 2 | 3 | 4 |
| Heart rate (BPM) | 100 | 98 | 96 | 102 |
| R-R interval (ms) | 600 | 610 | 620 | 590 |
| R-R (1/128 sec) | 76 | 78 | 79 | 75 |
| e (1/128 sec) | 52 | 50 | 49 | 53 |
| Limited e | 32 | 32 | 32 | 32 |
| Error | 2432 | 2496 | 2528 | 2400 |
| Integral | 2432 | 4928 | 7456 | 9856 |
| PPT | 0 | 1 | 1 | 2 |

In an embodiment of the present invention, the heart rate regulation algorithm corrects for missed heart beats (either of physiological origin or because of a failure to detect a beat). Typically, to perform this correction, any R-R interval which is about twice as long as the immediately preceding R-R interval is interpreted as two R-R intervals, each having a length equal to half the measured interval. For example, the R-R interval sequence (measured in seconds) 1, 1, 1, 2.2 is interpreted by the algorithm as the sequence 1, 1, 1, 1.1, 1.1. Alternatively or additionally, the algorithm corrects for premature beats, typically by adjusting the timing of beats that do not occur approximately halfway between the preceding and following beats. For example, the R-R interval sequence (measured in seconds) 1, 1, 0.5, 1.5 is interpreted as 1, 1, 1, 1, using the assumption that the third beat was premature.

In an embodiment of the present invention, control unit 20 is configured to operate in one of the following modes:
- vagal stimulation is not applied when the heart rate of the subject is lower than the low end of the normal range of a heart rate of the subject and/or of a typical human subject;
- vagal stimulation is not applied when the heart rate of the subject is lower than a threshold value equal to the current low end of the range of the heart rate of the subject, i.e., the threshold value is variable over time as the low end generally decreases as a result of chronic vagal stimulation treatment;
- vagal stimulation is applied only when the heart rate of the subject is within the normal of range of a heart rate of the subject and/or of a typical human subjects;
- vagal stimulation is applied only when the heart rate of the subject is greater than a programmable threshold value, such as a rate higher than a normal rate of the subject and/or a normal rate of a typical human subject. This mode generally removes peaks in heart rate; or
- vagal stimulation is applied using fixed programmable parameters, i.e., not in response to any feedback, target heart rate, or target heart rate range. These parameters may be externally updated from time to time, for example by a physician.

In an embodiment of the present invention, the amplitude of the applied stimulation current is calibrated by fixing a number of pulses in the series of pulses (per cardiac cycle), and then increasing the applied current until a desired predetermined heart rate reduction is achieved. Alternatively, the current is calibrated by fixing the number of pulses per series of pulses, and then increasing the current to achieve a substantial reduction in heart rate, e.g., 40%.

In embodiments of the present invention in which vagal stimulation system 18 comprises implanted device 25 for monitoring and correcting the heart rate, control unit 20 typically uses measured parameters received from device 25 as additional inputs for determining the level and/or type of stimulation to apply. Control unit 20 typically coordinates its behavior with the behavior of device 25. Control unit 20 and device 25 typically share sensors 28 in order to avoid redundancy in the combined system.

Optionally, vagal stimulation system 18 comprises a patient override, such as a switch that can be activated by the subject using an external magnet. The override typically can be used by the subject to activate vagal stimulation, for example in the event of arrhythmia apparently undetected by the system, or to deactivate vagal stimulation, for example in the event of apparently undetected physical exertion.

Figure 4:
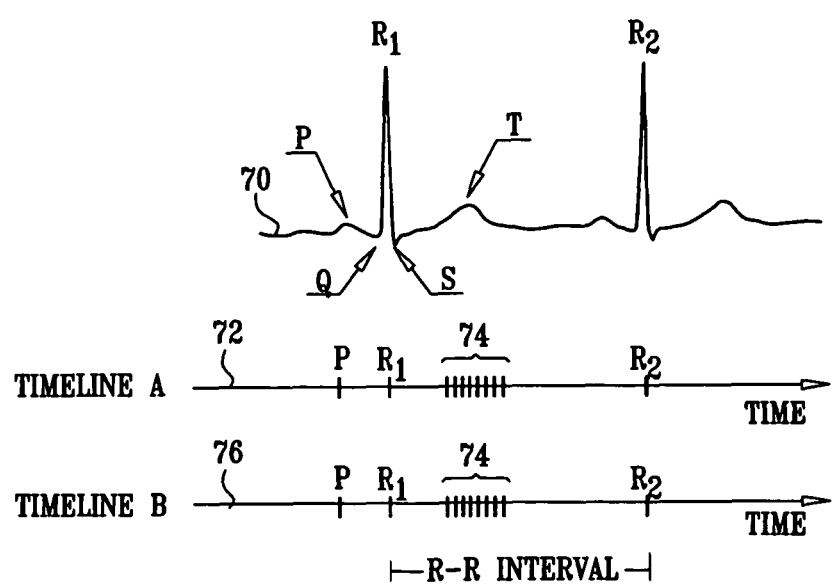
FIG. 4 is a simplified illustration of an electrocardiogram (ECG) recording and of example timelines showing the timing of the application of a series of stimulation pulses, in accordance with an embodiment of the present invention.

FIG. 4 is a simplified illustration of an ECG recording 70 and example timelines 72 and 76 showing the timing of the application of a burst of stimulation pulses 74, in accordance with an embodiment of the present invention. Stimulation is typically applied to vagus nerve 36 in a closed-loop system in order to achieve and maintain the desired target heart rate, determined as described above. Precise graded slowing of the heart beat is typically achieved by varying the number of nerve fibers stimulated, in a smaller-to-larger diameter order, and/or the intensity of vagus nerve stimulation, such as by changing the stimulation amplitude, pulse width, PPT, and/or delay. Stimulation with blocking, as described herein, is typically applied during each cardiac cycle in burst of pulses 74, typically containing between about 1 and about 20 pulses, each of about 1-3 milliseconds duration, over a period of about 1-200 milliseconds. Advantageously, such short pulse durations generally do not substantially block or interfere with the natural efferent or afferent action potentials traveling along the vagus nerve. Additionally, the number of pulses and/or their duration is sometimes varied in order to facilitate achievement of precise graded slowing of the heart beat.

In an embodiment of the present invention (e.g., when the heart rate regulation algorithm described hereinabove is not implemented), to apply the closed-loop system, the target heart rate is expressed as a ventricular R-R interval (shown as the interval between $R_1$ and $R_2$ in FIG. 4). The actual R-R interval is measured in real time and compared with the target R-R interval. The difference between the two intervals is defined as a control error. Control unit 20 calculates the change in stimulation necessary to move the actual R-R towards the target R-R, and drives electrode device 26 to apply the new calculated stimulation. Intermittently, e.g., every 1, 10, or 100 beats, measured R-R intervals or average R-R intervals are evaluated, and stimulation of the vagus nerve is modified accordingly.

In an embodiment, vagal stimulation system 18 is further configured to apply stimulation responsive to pre-set time parameters, such as intermittently, constantly, or based on the time of day.

Alternatively or additionally, one or more of the techniques of smaller-to-larger diameter fiber recruitment, selective fiber population stimulation and blocking, and varying the intensity of vagus nerve stimulation by changing the stimulation amplitude, pulse width, PPT, and/or delay, are applied in conjunction with methods and apparatus described in one or more of the patents, patent applications, articles and books cited herein.

In an embodiment of the present invention, control unit 20 comprises or is coupled to an implanted device 25 for monitoring and correcting the heart rate, such as an implantable cardioverter defibrillator (ICD) or a pacemaker (e.g., a biventricular or standard pacemaker). For example, implanted device 25 may be incorporated into a control loop executed by control unit 20, in order to increase the heart rate when the heart rate for any reason is too low.

In an embodiment of the present invention, a method for increasing vagal tone comprises applying signals to vagus nerve 36, and configuring the signals to stimulate the vagus nerve, thereby delivering parasympathetic nerve stimulation to heart 30, while at the same time minimizing the heart-rate-lowering effects of the stimulation. Such treatment generally results in the beneficial effects of vagal stimulation that are not necessarily dependent on the heart-rate reduction effects of such stimulation. (See, for example, the above-cited article by Vanoli E et al.)

In an embodiment of the present invention, in order to increase vagal tone while at the same time minimizing or preventing the heart-rate-lowering effects of the stimulation, control unit 20 applies the signals to the vagus nerve as a burst of pulses during each cardiac cycle, with one or more of the following parameters:

Timing of the stimulation: delivery of the burst of pulses begins after a variable delay following each P-wave, the length of the delay equal to between about two-thirds and about 90% of the length of the patient's cardiac cycle. Such a delay is typically calculated on a real-time basis by continuously measuring the length of the patient's cardiac cycle.

Pulse duration: each pulse typically has a duration of between about 200 microseconds and about 2.5 milliseconds for some applications, or, for other applications, between about 2.5 milliseconds and about 5 milliseconds.

Pulse amplitude: the pulses are typically applied with an amplitude of between about 0.5 and about 5 milliamps, e.g., about 1 milliamp.

Pulse repetition interval: the pulses within the burst of pulses typically have a pulse repetition interval (the time from the initiation of a pulse to the initiation of the following pulse) of between about 2 and about 10 milliseconds, e.g., about 2.5 milliseconds.

Pulse period: the burst of pulses typically has a total duration of between about 0.2 and about 40 milliseconds, e.g., about 1 millisecond.

Pulses per trigger (PPT): the burst of pulses typically contains between about 1 and about 10 pulses, e.g., about 2 pulses.

Vagus nerve: the left vagus nerve is typically stimulated in order to minimize the heart-rate-lowering effects of vagal stimulation.

Duty cycle: stimulation is typically applied only once every several heartbeats (or once per heartbeat, when a stronger effect is desired).

On/off status: for some applications, stimulation is always "on", i.e., constantly applied (in which case, parameters closer to the lower ends of the ranges above are typically used). For other applications, on/off cycles vary between a few seconds to several dozens of seconds, e.g., "on" for about 36 seconds, "off" for about 120 seconds, "on" for about 3 seconds, "off" for about 9 seconds.

For example, vagal stimulation may be applied to a patient having a heart rate of 60 BPM, with the intention of minimally reducing the patient's heart rate. The burst of pulses may be delivered beginning about 750 milliseconds after each R-wave of the patient. The stimulation may be applied with one pulse per trigger (PPT), and having an amplitude of 1 milliamp. The stimulation may be cycled between "on" and "off" periods, with each "on" period having a duration of about two seconds, i.e., two heart beats, and each "off" period having a duration of about 4 seconds.

Alternatively or additionally, implanted device 25 comprises a pacemaker, as described hereinabove with reference to FIG. 1, and control unit 20 drives the pacemaker to pace heart 30, so as to prevent any heart-rate lowering effects of such vagal stimulation. Typically, the control unit paces the heart at a rate that is similar to the rate when the device is in "off" mode. Control unit 20 then applies signals to vagus nerve 36, typically using the typical stimulation parameters described in the above-referenced U.S. patent application Ser. No. 10/866,601, filed Jun. 10, 2004, entitled, "Applications of vagal stimulation." This vagal stimulation generally does not lower the heart rate, because of the pacemaker pacing. For some applications, control unit 20 applies signals to vagus nerve 36, and senses the heart rate after applying the signals. The control unit drives the pacemaker to pace the heart if the sensed heart rate falls below a threshold heart rate. The threshold heart rate is typically equal to a heart rate of the patient prior to commencing the vagal stimulation, for example, as sensed by control unit 20. The control unit thus typically maintains the heart rate at a rate above a bradycardia threshold rate, unlike conventional pacemakers which are typically configured to pace the heart only when the rate falls below a bradycardia threshold rate. Upon termination of vagal stimulation, control unit 20 typically drives the pacemaker to continue pacing the heart for a period typically having a duration between about 0 and about 30 seconds, such as about 5 seconds.

In an embodiment of the present invention, vagal stimulation system 18 is adapted to be used prior to, during, and/or following a clinical procedure. Control unit 20 drives electrode device 26 to apply vagal stimulation, and typically configures the stimulation to reduce a potential immune-mediated response to the procedure. Such a reduction generally promotes healing after the procedure. (See Borovikova L V et al. cited hereinabove, which describe an anti-inflammatory cholinergic pathway that may mediate this reduction in immune-related response.) When the procedure is heart-related, the vagal stimulation additionally typically reduces mechanical stress by lowering heart rate and pressures, reduces heart rate, and/or improves coronary blood flow.

For some applications, the vagal stimulation commences after the conclusion of the procedure. For some applications, the vagal stimulation commences prior to the commencement of the procedure. Alternatively, the stimulation commences during the procedure. Further alternatively, the stimulation is applied before and after the procedure, but not during the procedure.

For some applications, the clinical procedure is selected from one of the following:

- coronary artery bypass graft (CABG) surgery. In addition to the benefits of vagal stimulation described above, vagal tone was shown by Cumming J E et al. (cited hereinabove) to be effective in reducing the likelihood of postoperative atrial fibrillation (AF), increasing the likelihood that the graft will stay in place, reducing the likelihood of graft failure (e.g., via stenosis), improving healing from the surgery, and/or reducing pain associated with the surgery. It is hypothesized by the inventors that such a reduction in the likelihood of postoperative AF is due, at least in part, to the mechanical stress reduction and rhythmic vagal activity promoted by vagal stimulation. For some applications, the vagal stimulation is applied for between 1 and 7 days after the CABG surgery, intermittently or continuously.
- valve replacement surgery. In addition to the benefits of vagal stimulation described above, vagal stimulation generally reduces the likelihood of postoperative AF, promotes healing of the heart, and reduces the likelihood of other conductance abnormalities.
- heart transplantation. In addition to the benefits of vagal stimulation described above, vagal stimulation generally reduces the likelihood of rejection of the transplanted heart. For some applications, vagal stimulation is applied on a short-term basis, e.g., for less than about 7 days before and/or 7 days after the heart transplantation. Alternatively, vagal stimulation is applied long-term, e.g., for more than about 2 weeks before and/or 2 weeks after the procedure.
- other organ transplantation, such as kidney, liver, skin grafting, and bone marrow transplantation. In addition to the benefits of vagal stimulation described above, vagal stimulation generally reduces the likelihood of rejection of the transplanted organ.
- percutaneous transluminal coronary angioplasty (PTCA) and/or stenting procedures. In addition to the benefits of vagal stimulation described above, vagal stimulation generally reduces the likelihood of restenosis, which is believed to be at least in part immune-mediated. In addition, vagal stimulation induces coronary dilation, which generally reduces the likelihood of restenosis.
- carotid endarterectomy. In addition to the benefits of vagal stimulation described above, vagal stimulation generally reduces the likelihood of restenosis, which is believed to be at least in part immune-mediated.
- other bypass surgery. In addition to the benefits of vagal stimulation described above, vagal stimulation generally reduces the likelihood of restenosis in the grafted bypass (natural or artificial).
- abdominal surgery. In addition to the benefits of vagal stimulation described above, vagal stimulation generally reduces the likelihood of narrowing of parts of the GI tract (a complication that often occurs after GI surgery, especially when anastomosis of GI components is performed).

In an embodiment of the present invention, control unit 20 drives electrode device 26 to apply vagal stimulation, and configures the stimulation to reduce hyperactivity or activity of brain cells, in order to treat conditions such as stroke and Attention Deficit Hyperactivity Disorder (ADHD). In one application, secondary stroke damage to cells in areas adjacent to the hypoxic area may be reduced by reducing the cell activity in these areas. In another application, vagal stimulation is configured to help reduce hyperactivity and improve concentration of a subject suffering from ADHD.

In an embodiment of the present invention, control unit 20 drives electrode device 26 to apply vagal stimulation, and configures the stimulation to treat one of the following conditions by reducing immune system hyperactivation associated with the condition:

- vasculitis, e.g., Wegener granulomatosis, temporal arteritis, Takayasu arteritis, and/or polyarteritis nodosa;
- systemic sclerosis;
- systemic lupus erythematosus;
- flare of Crohn's disease;
- flare of ulcerative colitis;
- autoimmune hepatitis;
- glomerulonephritis;
- arthritis, e.g., reactive or rheumatoid;
- pancreatitis;
- thyroiditis;
- idiopathic thrombocytopenic purpura (ITP);
- thrombotic thrombocytopenic purpura (TTP);
- multi-organ failure associated with sepsis (especially gram negative sepsis);
- anaphylactic shock;
- Acute Respiratory Distress Syndrome (ARDS);
- asthma;
- an allergy—vagal stimulation is applied to attenuate allergic reactions of subjects suffering from acquired sensitizations to drugs or allergens, or from intense allergies. For some applications, vagal stimulation system 18 is configured to be an on-demand therapeutic adjuvant, e.g., to reduce the need for drug therapy; or
- multiple sclerosis.

In an embodiment of the present invention, control unit 20 drives electrode device 26 to apply vagal stimulation, and configures the stimulation to treat a habitual behavior or a condition associated with a habitual behavior. The inventors hypothesize that vagal stimulation is effective for treating such behavior because the stimulation interferes with acquired habits or routines of the central nervous system (CNS). For some application, control unit 20 drives the electrode device to apply the stimulation at non-constant intervals, such as at random, quasi-random, or seemingly random intervals (e.g., generated using a random number generator or using a preselected set or pattern of varying intervals). The use of such variable intervals breaks cycles of the CNS responsible for such habitual behaviors. The use of non-constant intervals typically reduces the likelihood of the CNS cycle becoming synchronized with the stimulation, i.e., reduces the likelihood of accommodation.

Such habitual behaviors or behavior-related conditions include, but are not limited to:

- anorexia, such as anorexia nervosa;
- smoking;
- drug addiction;
- obsessive compulsive disorders;
- intractable hiccups
- sleep apnea;
- Tourette syndrome; and
- hiccups.

In an embodiment of the present invention, control unit 20 drives electrode device 26 to apply vagal stimulation that shifts the balance of the autonomic nervous system towards the parasympathetic side thereof, so as to modify the allocation of body resources among different organs and functions. Such vagal stimulation antagonizes the sympathetic system and augments the parasympathetic system, and may be applied in order to treat one or more of the following conditions:

- hyperlipidemia—vagal stimulation is applied to promote lipid metabolism and absorption by the liver, and antagonizes the carbohydrate-based sympathetically-derived metabolism;
- insulin resistance (e.g., type II diabetes)—the sympathetic system generally drives muscle tissue to increase its sensitivity to insulin. Vagal stimulation is applied to augment the parasympathetic system, thereby reducing the short-term sensitivity of muscle tissue to insulin. As a result, the long-term insulin sensitivity of muscle tissue increases;
- chronic renal failure—vagal stimulation is applied to increase renal blood flow and glomerular filtration rate (GFR) by reducing blood flow to skeletal muscle (which blood flow is augmented by the sympathetic system), thereby allowing more blood to reach the kidneys, at lower pressures. For some applications, the vagal stimulation is applied while the patient sleeps, or is physically inactive, during which times the need for blood flow to skeletal muscle is reduced. Alternatively or additionally, vagal stimulation increases the GFR by acting on the kidney vascular bed;
- chronic hepatic failure—vagal stimulation is applied to increase blood flow through the portal vein by reducing blood flow to skeletal muscle, thereby increasing blood flow through the liver. As a result, a compromised liver is able to perform additional work, and the condition of the patient improves. For some applications, the vagal stimulation is applied while the patient sleeps, or is physically inactive, during which times the need for blood flow to skeletal muscle is reduced;
- insomnia—vagal stimulation is applied to shift the autonomic balance towards the parasympathetic system, allowing the mind and body to relax. Vagal stimulation promotes activities such as digestion, relaxation, and sleep;
- muscle fatigue (such as associated with heart failure)—vagal stimulation is applied to reduce blood flow and energy consumption of skeletal muscles, thus allowing for muscle rest and recovery (similar to the manner in which beta blockers assist failing hearts);
- muscle hypertonia—vagal stimulation is applied to reduce the tension in skeletal muscles, and/or to reduce the symptoms of hypertonia, such as hypertonia associated with upper motor neuron lesions;
- sexual dysfunction—vagal stimulation is applied to increase the sensitivity of the sexual organs by increasing parasympathetic input, thereby promoting improved sexual function and/or pleasure;
- anemia due to reduced production of red blood cells—vagal stimulation is applied to promote increased medullar red blood cell production and/or extramedullary red blood cell production. In unpublished data obtained from chronically vagal stimulated dogs, the inventors have shown increased extramedullary red blood cell production in response to chronic vagal stimulation; or
- reduced peripheral blood flow—in contrast to the sympathetic system that augments blood flow to skeletal muscle, vagal stimulation reduces blood flow to skeletal muscle, thus augmenting the flow in peripheral blood vessels. In addition, parasympathetic stimulation has a direct effect of vasodilatation on peripheral blood vessels, further augmenting peripheral blood flow.

In an embodiment of the present invention, vagal stimulation is applied to treat stroke of a subject, such as by causing vasodilation. For some applications, such vagal stimulation is applied responsively to one or more sensed physiological parameters.

In an embodiment of the present invention, vagal stimulation is applied to treat a condition of a subject by regulating cell division of the subject. For some applications, the stimulation is configured to increase cell division to treat conditions including, but not limited to:

- anemia;
- a neurodegenerative disease;
- liver cirrhosis;
- an immune deficiency;
- a skin burn or abrasion;
- a muscle degenerative disorder;
- cardiac failure; and
- a reproductive system disorder.

For some applications, the stimulation is configured to decrease cell division to treat conditions including, but not limited to:

- a neoplastic disorder;
- a hematologic malignancy; and
- polycythemia vera.

It has been suggested that cell cycle regulation is one of the humoral functions regulated by the vagus nerve. Preliminary data from animal experiments conducted by the inventors suggest that the vagus nerve regulates cell division. Such data include the incidence of splenomegaly in vagally-stimulated laboratory animals, and histological data from harvested cardiac tissue showing reduced levels of fibroblast growth among vagally-stimulated laboratory animals.

For some applications, when performing the vagal stimulation techniques described herein, vagal stimulation is applied for several hours, several days, several weeks, or longer. For some applications in which the vagal stimulation is applied on a short-term basis, a stimulating electrode is positioned in a manner that enables the expulsion of the electrode at the conclusion of the vagal stimulation treatment period. For some applications, the stimulating electrode is placed using a meltable or dissolvable suture or other element, which, when melted or dissolved at the completion of the treatment period, enables the electrode to be removed.

In an embodiment of the present invention, all or a portion of the electrode assembly, including conductive elements, is adapted to be dissolvable. When the dissolvable portion of the electrode assembly dissolves, the electrode assembly comes loose from the nervous tissue (e.g., the nerve), and the non-dissolvable portion of the electrode assembly, if any, can be removed. Appropriate dissolvable materials include polyglycolic acid (PGA) or poly(L-lactide) acid (PLL). For some applications, the portion of the electrode assembly that is within about 2 cm of the nervous tissue (e.g., the nerve) comprises entirely non-metal components, all or a portion of which are dissolvable. For some applications, the electrode assembly comprises electrode leads comprising metal wires, which are used to conduct the current through the body until a distance of about 2 cm from the nervous tissue (e.g., the nerve). For some applications, for conducting the current within about 2 cm of the nervous tissue (e.g., the nerve), the electrode assembly comprises electrode leads which comprise tubes (which are typically dissolvable) that contain an electrically conductive biologically-compatible liquid, such as saline solution. For some applications, in order to determine whether the dissolvable portion of the electrode assembly has dissolved sufficiently to enable safe removal of the remainder of the electrode assembly, the impedance of the assembly is measured.

In an embodiment of the present invention, vagal stimulation system 18 comprises an external stimulator, such as when a short period of activation is required. After completion of treatment, the external stimulator is disconnected from the subject, leaving only the electrodes implanted in the subject. For some applications, all or a portion of the electrodes dissolve, as described above, and/or all or a portion of the electrodes are removed from the subject. For some applications, vagal stimulation system 18 additionally comprises an external sensing element, such as an electrocardiogram (ECG) monitor, an electroencephalogram (EEG) monitor, a pulse oximeter, an ultrasound system, an MRI imaging system, a capnograph, a temperature sensor, a blood glucose monitor, a blood lipid monitor, a blood lactic acid monitor, or a blood urea, creatinine, or ammonia level monitor. For some applications, the external stimulator is adapted to be placed together with attached electrical leads in a sterile bag attached to the body at the site of insertion, which generally reduces the likelihood of infection.

In an embodiment of the present invention, vagal stimulation system 18 comprises an implantable stimulator comprising an internal battery. Alternatively or additionally, the implantable stimulator is powered with electromagnetically induced current, using an inducer external to the body. Further alternatively, vagal stimulation system 18 comprises one or more implantable electrodes that are activated by an external stimulator via magnetic induction.

In an embodiment of the present invention, vagal stimulation system 18 comprises a mechanical vibrator adapted to be placed external to the body, and to apply carotid massage in order to increase parasympathetic tone.

In an embodiment of the present invention, vagal stimulation system 18 comprises at least one electrode that is adapted to be positioned using vascular catheterization. For example, techniques described in one or more of the following articles may be used:

Vago H et al., "Parasympathetic cardiac nerve stimulation with implanted coronary sinus lead," J Cardiovasc Elect 15:588-590 (2004)

Kara J et al., "Identification and characterization of atrioventricular parasympathetic innervation in humans," Cardiovasc Elect 13:735-739 (2002)

Kara J. et al., "Characterization of sinoatrial parasympathetic innervation in humans," J Cardiovasc Elect 10:1060-1065 (1999)

In an embodiment of the present invention, control unit 20 is configured to apply the vagal stimulation described hereinabove using one or more of the following techniques:

Control unit 20 configures the stimulation to be applied constantly, with a stimulation frequency between about 0.1 Hz and about 100 Hz, e.g., between about 0.1 Hz and about 5 Hz, or between about 5 Hz and about 100 Hz.

Control unit 20 synchronizes the stimulation with the cardiac cycle of subject 31, such as by using techniques described hereinabove and/or in one or more of the applications incorporated herein by reference.

Control unit 20 configures the stimulation using the minimal-heart-rate-lowering parameters described hereinabove.

Control unit 20 applies the stimulation only when the heart rate is above a threshold value, which is typically less than the average heart rate of subject 31, or less than the average heart rate of a typical subject.

Control unit 20 applies the stimulation intermittently, such as by using techniques described hereinabove and/or in one or more of the applications incorporated herein by reference.

Control unit 20 is configured to provide manual control of one or more of the stimulation parameters.

For some applications, techniques described herein are used to apply controlled stimulation to one or more of the following: the lacrimal nerve, the salivary nerve, the vagus nerve, the pelvic splanchnic nerve, or one or more sympathetic or parasympathetic autonomic nerves. Such controlled stimulation may be applied to such nerves directly, or indirectly, such as by stimulating an adjacent blood vessel or space. Such controlled stimulation may be used, for example, to regulate or treat a condition of the lung, heart, stomach, pancreas, small intestine, liver, spleen, kidney, bladder, rectum, large intestine, reproductive organs, or adrenal gland.

As appropriate, techniques described herein are practiced in conjunction with methods and apparatus described in one or more of the following patent applications, all of which are assigned to the assignee of the present application and are incorporated herein by reference:

U.S. patent application Ser. No. 10/205,474, filed Jul. 24, 2002, entitled, "Electrode assembly for nerve control," which issued as U.S. Pat. No. 6,907,295

U.S. Provisional Patent Application 60/383,157 to Ayal et al., filed May 23, 2002, entitled, "Inverse recruitment for autonomic nerve systems"

U.S. patent application Ser. No. 10/205,475, filed Jul. 24, 2002, entitled, "Selective nerve fiber stimulation for treating heart conditions," which published as US Patent Publication 2003/0045909

PCT Patent Application PCT/IL02/00068, filed Jan. 23, 2002, entitled, "Treatment of disorders by unidirectional nerve stimulation," and U.S. patent application Ser. No. 10/488,334, filed Feb. 27, 2004, in the US National Phase thereof U.S. patent application Ser. No. 09/944,913, filed Aug. 31, 2001, entitled, "Treatment of disorders by unidirectional nerve stimulation," which issued as U.S. Pat. No. 6,684,105

U.S. patent application Ser. No. 10/461,696, filed Jun. 13, 2003, entitled, "Vagal stimulation for anti-embolic therapy"

PCT Patent Application PCT/IL03/00430, filed May 23, 2003, entitled, "Electrode assembly for nerve control," which published as PCT Publication WO 03/099373, and U.S. patent application Ser. No. 10/529,149, in the national stage thereof PCT Patent Application PCT/IL03/00431, filed May 23, 2003, entitled, "Selective nerve fiber stimulation for treating heart conditions," which published as PCT Publication WO 03/099377

U.S. patent application Ser. No. 10/719,659, filed Nov. 20, 2003, entitled, "Selective nerve fiber stimulation for treating heart conditions"

A PCT patent application filed May 23, 2004, entitled, "Selective nerve fiber stimulation for treating heart conditions"

A PCT patent application filed Jun. 10, 2004, entitled, "Applications of vagal stimulation"

A US patent application filed Jun. 10, 2004, entitled, "Applications of vagal stimulation"

A PCT patent application filed Jun. 10, 2004, entitled, "Vagal stimulation for anti-embolic therapy"

U.S. Provisional Patent Application 60/478,576, filed Jun. 13, 2003, entitled, "Applications of vagal stimulation"

U.S. patent application Ser. No. 09/824,682 to Cohen and Ayal, filed Apr. 4, 2001, entitled "Method and apparatus for selective control of nerve fibers"

U.S. patent application Ser. No. 11/022,011 to Cohen et al., filed Dec. 22, 2004, entitled, "Construction of electrode assembly for nerve control"

U.S. patent application Ser. No. 11/234,877 to Ben-David et al., filed Sep. 22, 2005, entitled, "Selective nerve fiber stimulation"

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A treatment method, comprising:
   identifying a subject as one who is selected to undergo an interventional medical procedure; and
   in response to the identifying, reducing a likelihood of a potential adverse effect of the procedure, wherein the potential adverse effect is postoperative atrial fibrillation, by applying an electrical current to a parasympathetic site of the subject selected from the group consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a jugular vein of the subject, a right ventricle of the subject, a parasympathetic ganglion of the subject, and a parasympathetic nerve of the subject,
   wherein applying the current comprises commencing applying the current after the subject concludes undergoing the procedure.

2. The method according to claim 1, wherein the postoperative atrial fibrillation includes an immune-mediated response to the procedure, and wherein applying the current comprises configuring the current to reduce the likelihood of the immune-mediated response.

3. The method according to claim 1, wherein applying the current comprises commencing applying the current within the first 7 days after the subject concludes undergoing the procedure.

4. The method according to claim 1, wherein the interventional procedure includes a heart procedure, and wherein identifying the subject comprises identifying the subject as one who is selected to undergo the heart procedure.

5. The method according to claim 4, wherein applying the current comprises configuring the current to reduce mechanical stress of the heart.

6. The method according to claim 4, wherein applying the current comprises configuring the current to reduce a heart rate of the subject.

7. The method according to claim 4, wherein applying the current comprises configuring the current to improve coronary blood flow of the subject.

8. The method according to claim 4, wherein the heart procedure includes coronary bypass surgery, and wherein identifying the subject comprises identifying the subject as one who is selected to undergo the coronary bypass surgery.

9. The method according to claim 8, wherein applying the current comprises configuring the current to reduce a likelihood of graft failure.

10. The method according to claim 8, wherein applying the current comprises configuring the current to reduce a likelihood of a reduction of peripheral blood flow.

11. The method according to claim 4, wherein the heart procedure includes carotid endarterectomy, and wherein identifying the subject comprises identifying the subject as one who is selected to undergo the carotid endarterectomy.

12. The method according to claim 11, wherein applying the current comprises configuring the current to reduce a likelihood of restenosis.

13. The method according to claim 1, wherein the interventional procedure includes a surgical procedure, and wherein identifying the subject comprises identifying the subject as one who is selected to undergo the surgical procedure.

14. The method according to claim 13, wherein the surgical procedure includes a surgical heart procedure, and wherein identifying the subject comprises identifying the subject as one who is selected to undergo the surgical heart procedure.

15. The method according to claim 13, wherein the interventional procedure includes an abdominal surgical procedure, and wherein identifying the subject comprises identifying the subject as one who is selected to undergo the abdominal surgical procedure.

16. The method according to claim 15, wherein applying the current comprises configuring the current to reduce a likelihood of a complication selected from the group consisting of: stenosis of gastrointestinal (GI) tract segments involved in the surgical procedure, GI stasis, and flare of inflammatory disease.

17. The method according to claim 13, wherein the interventional procedure includes transplantation of tissue selected from the group consisting of: an organ and cells, and wherein identifying the subject comprises identifying the subject as one who is selected to undergo the transplantation of the selected tissue.

18. The method according to claim 13, wherein the interventional procedure includes implantation of an implantable medical device, and wherein identifying the subject comprises identifying the subject as one who is selected to undergo the implantation of the device.

19. The method according to claim 13, wherein the interventional procedure includes a heart transplantation procedure, and wherein identifying the subject comprises identifying the subject as one who is selected to undergo the heart transplantation procedure.

20. The method according to claim 19, wherein applying the current comprises concluding application of the current at least 2 weeks after the heart transplantation procedure.

21. The method according to claim 13, wherein the surgical procedure includes a cardiac procedure selected from the group consisting of: a valve replacement procedure, and a valvoplasty procedure, and wherein identifying the subject comprises identifying the subject as one who is selected to undergo the selected cardiac procedure.

22. The method according to claim 13, wherein the surgical procedure includes a percutaneous transluminal coronary angioplasty (PTCA) procedure, and wherein identifying the subject comprises identifying the subject as one who is selected to undergo the PTCA procedure.

23. The method according to claim 22, wherein the potential adverse effect includes restenosis, and wherein reducing the likelihood comprises reducing the likelihood of the restenosis.

* * * * *